US010537739B2

(12) United States Patent
Vanpoucke et al.

(10) Patent No.: US 10,537,739 B2
(45) Date of Patent: Jan. 21, 2020

(54) ELECTRODE SELECTION

(71) Applicant: Cochlear Limited, Macquarie University, NSW (AU)

(72) Inventors: Filiep J. Vanpoucke, Huldenberg (BE); Obaid ur Rehman Qazi, Mechelen (BE)

(73) Assignee: Cochlear Limited, Macquarie University, NSW (AU)

( * ) Notice: Subject to any disclaimer, the term of this patent is extended or adjusted under 35 U.S.C. 154(b) by 259 days.

(21) Appl. No.: 15/165,106

(22) Filed: May 26, 2016

(65) Prior Publication Data

US 2017/0340876 A1    Nov. 30, 2017

(51) Int. Cl.
*A61N 1/36* (2006.01)
*A61N 1/05* (2006.01)
(52) U.S. Cl.
CPC ....... *A61N 1/36038* (2017.08); *A61N 1/0541* (2013.01)
(58) Field of Classification Search
CPC .......................... A61N 1/36038; A61N 1/0541
See application file for complete search history.

(56) References Cited

U.S. PATENT DOCUMENTS

| 8,391,993 | B2 | 3/2013 | van den Honert et al. |
| 8,914,125 | B2 | 12/2014 | Vanpoucke |
| 2011/0093038 | A1 | 4/2011 | Honert |
| 2011/0200216 | A1 | 8/2011 | Lee et al. |
| 2012/0065705 | A1 | 3/2012 | Kals |
| 2015/0025596 | A1 | 1/2015 | Kals |
| 2015/0088225 | A1 | 3/2015 | Noble et al. |
| 2015/0251006 | A1 | 9/2015 | Qazi et al. |
| 2015/0258337 | A1 | 9/2015 | Long et al. |

FOREIGN PATENT DOCUMENTS

KR    101000168 B1    12/2010

OTHER PUBLICATIONS

International Search Report and Written Opinion for PCT/IB2017/053125, dated Sep. 8, 2017.
Jack H. Noble et al., "Clinical Evaluation of an Image-Guided Cochlear Implant Programming Strategy," Audiology & Neurotology, Nov. 7, 2014, pp. 400-411, vol. 19.

(Continued)

*Primary Examiner* — Paula J Stice
(74) *Attorney, Agent, or Firm* — Pilloff Passino & Cosenza LLP; Martin J. Cosenza

(57) ABSTRACT

A method, including the action of executing a first evaluation including evaluating first interactions of respective current spreads with one another for a plurality of first electrodes implanted in a recipient resulting from energizement thereof with at least one second implanted electrode disabled, wherein the second electrode, if enabled and energized at about the same level as at least one of the first electrodes, would result in current spread to at least one of the plurality of first electrodes, and one of disabling at least one third electrode of the plurality of first electrodes based on the evaluation or maintaining an enablement of the nondisabled electrodes based on the evaluation.

29 Claims, 26 Drawing Sheets

(56) References Cited

OTHER PUBLICATIONS

Monita Chatterjee et al., "A relation between electrode discrimination and amplitude modulation detection by cochlear implant listeners," Journal of the Acoustical Society of America, Jan. 2010, pp. 415-426, vol. 127, No. 1, Acoustical Society of America.

Shaza M Saleh et al., "Clinical use of electrode differentiation to enhance programming of cochlear implants," Cochlear Implants International, Nov. 2013, pp. S16-S18, vol. 14, No. S4.

Julie Arenberg Bierer et al., "Comparisons Between Detection Threshold and Loudness Perception for Individual Cochlear Implant Channels," Ear & Hearing, Nov. 2014, pp. 641-651, vol. 35, No. 6, Lippincott Williams & Wilkins.

- automatically determining which electrodes of the prosthesis to disable based on the evaluation with or without a processor;
- applying electrical current to the electrodes of the plurality of electrodes to determine current spreads or neural spreads either automatically or not
- automatically disabling or disadvantaging at least one electrode based on the evaluation
- automatically executing the action of evaluating at least one of the interactions of the respective current/neural spreads with one another
- evaluating interaction of current from at least two of the plurality of electrodes and not evaluating interaction of current from at least one other electrode of the plurality of electrodes

FIG. 24

2410

- disabling at least 2 electrodes based on the evaluation
- evaluating interaction of neural excitation resulting from energizement of at least two electrodes with respective electrodes of the plurality of electrodes
- disadvantaging the at least one electrode based on the evaluation
- disadvantaging the at least one electrode based on the evaluation and not disabling or disadvantaging at least one electrode
- obtaining data indicative of at least one of the respective current spreads or respective neural spreads for the plurality of electrodes includes obtaining respective neural spreads for the plurality of electrodes
- creating a map for the hearing prosthesis based on the evaluation and applying the map to the hearing prosthesis
- evaluating at least one of interactions of respective current/neural spreads with one another includes doing for at least 6 electrodes

- evaluating at least one of interactions of respective current spreads with one another or interactions of respective neural spreads with one another for a first and a second electrode implanted in the recipient;
- evaluating at least one of interactions of respective current spreads with one another or interactions of respective neural spreads with one another for a third and a fourth electrode implanted in the recipient;
- evaluating at least one of interactions of respective current spreads with one another or interactions of respective neural spreads with one another for a fifth and a sixth electrode implanted in the recipient;
- evaluating at least one of interactions of respective current spreads with one another or interactions of respective neural spreads with one another for a seventh and a eighth electrode implanted in the recipient;

- evaluating at least one of interactions of respective current spreads with one another or interactions of respective neural spreads with one another for a ninth and a tenth electrode implanted in the recipient; and

- evaluating at least one of interactions of respective current spreads with one another or interactions of respective neural spreads with one another for an eleventh and a twelfth electrode implanted in the recipient.

- evaluating at least one of interactions of respective current spreads with one another or interactions of respective neural spreads with one another for a thirteenth and a fourteenth electrode implanted in the recipient;

- evaluating at least one of interactions of respective current spreads with one another or interactions of respective neural spreads with one another for a fifteenth and a sixteenth electrode implanted in the recipient;
- evaluating at least one of interactions of respective current spreads with one another or interactions of respective neural spreads with one another for a seventeenth and an eighteenth electrode implanted in the recipient.
- not evaluating interaction of current from at least one other electrode with the respective electrodes of the plurality of electrodes.
- disabling resulting from energizement thereof with at least the second electrode and a third electrode disabled, wherein the third electrode, if enabled and energized at about the same level as at least one of the first electrodes would result in current spread to at least one of the plurality of first electrodes;

- the action of evaluating at least one of interactions of respective current spreads with one another or interactions of respective neural spreads with one another for a plurality of electrodes implanted in a recipient is executed with at least one second implanted electrode disabled; and the method further comprises, prior to the action of evaluating, executing a second evaluation including evaluating second interaction of respective current spreads with one another for a plurality of electrodes including the plurality of electrodes and the at least one second electrode in a non-disabled state, and
- disabling the at least one second electrode based on the second evaluation.

- disabling at least fourth electrode based on the third evaluation; or maintaining an enablement of the nondisabled electrodes based on the third evaluation.
- obtaining data indicative of respective current spreads for the plurality of electrodes by: applying respective stimulation currents to respective electrodes in temporally non-overlapping manner; and
- obtaining data indicative of transimpedance at respective electrodes while the respective stimulation currents are applied.
- automatically comparing the data indicative of transimpedance for the respective electrodes for the respective stimulation currents.

- automatically developing weighting factors for the first electrodes based on the comparison of the data indicative of transimpedance for the respective first electrodes; and
- automatically determining which of the plurality of electrodes are to be disabled based on the weighting factors; and
- automatically disabling the determined electrodes.

ELECTRODE SELECTION

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. One example of a hearing prosthesis is a cochlear implant.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from hearing loss typically receive an acoustic hearing aid. Conventional hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve. Cases of conductive hearing loss typically are treated by means of bone conduction hearing aids. In contrast to conventional hearing aids, these devices use a mechanical actuator that is coupled to the skull bone to apply the amplified sound.

In contrast to hearing aids, which rely primarily on the principles of air conduction, certain types of hearing prostheses commonly referred to as cochlear implants convert a received sound into electrical stimulation. The electrical stimulation is applied to the cochlea, which results in the perception of the received sound.

It is noted that in at least some instances, there is utilitarian value to fitting a hearing prosthesis to a particular recipient. In some examples of some fitting regimes, there are methods which entail a clinician or some other professional presenting sounds to a recipient of the hearing prosthesis such that the hearing prosthesis evokes a hearing percept. Information can be obtained from the recipient regarding the character of the resulting hearing percept. Based on this information, the clinician can adjust or otherwise establish settings of the hearing prosthesis such that the hearing prosthesis operates according to these settings during normal use.

SUMMARY

In accordance with an exemplary embodiment, there is a method, comprising evaluating least one of interactions of respective current spreads with one another or interactions of respective neural spreads with one another for a plurality of electrodes implanted in a recipient, and disabling or disadvantaging at least one electrode based on the evaluation.

In accordance with an exemplary embodiment, there is a method, comprising executing a first evaluation including evaluating first interactions of respective current spreads with one another for a plurality of first electrodes implanted in a recipient resulting from energizement thereof with at least one second implanted electrode disabled, wherein the second electrode, if enabled and energized at about the same level as at least one of the first electrodes, would result in current spread to at least one of the plurality of first electrodes, and one of disabling at least one third electrode of the plurality of first electrodes based on the evaluation or maintaining an enablement of the nondisabled electrodes based on the evaluation.

In accordance with an exemplary embodiment, there is a fitting system, comprising a first sub-system configured to obtain respective spread function data for respective electrodes implanted in a recipient and a second sub-system configured to automatically evaluate the data; and a third sub-system configured to configure a hearing prosthesis based on the evaluation, wherein the configuration of the hearing prosthesis results in the deactivation of at least one of the implanted electrodes.

In accordance with an exemplary embodiment, there is a non-transitory computer readable medium having recorded thereon, a computer program for executing a method, the program including code for automatically determining which electrodes of a prosthesis to disable based on spread functions within a recipient.

BRIEF DESCRIPTION OF THE DRAWINGS

Embodiments are described below with reference to the attached drawings, in which:

FIGS. 23-30 contain schematics detailing various method actions according to exemplary embodiments.

DETAILED DESCRIPTION

Figure 1:
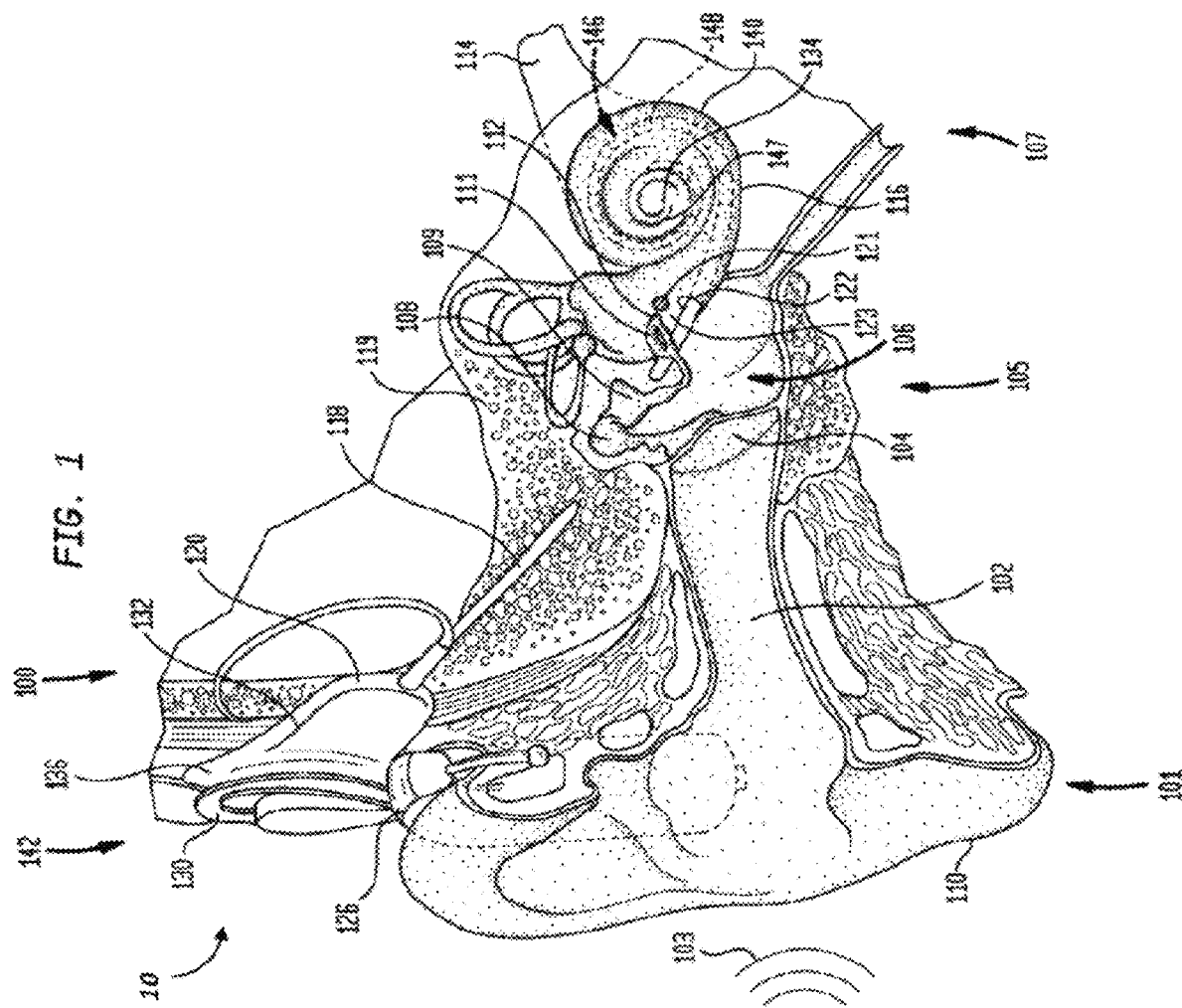
FIG. 1 is a perspective view of an exemplary hearing prosthesis in which at least some of the teachings detailed herein are applicable.

FIG. 1 is a perspective view of a cochlear implant, referred to as cochlear implant 100, implanted in a recipient, to which some embodiments detailed herein and/or variations thereof are applicable. It is briefly noted that while the embodiments detailed herein are described in terms of a cochlear implant, the teachings detailed herein are also applicable to other types of devices that utilize electrodes implanted in the recipient to stimulate tissue. By way of example only and not by way of limitation, in an exemplary embodiment, the teachings detailed herein can be applicable to a retinal implant and/or a pacemaker or other muscle stimulator device.

The cochlear implant 100 is part of a system 10 that can include external components, in some embodiments, as will be detailed below. It is noted that the teachings detailed herein are applicable, in at least some embodiments, to partially implantable and/or totally implantable cochlear implants (i.e., with regard to the latter, such as those having an implanted microphone). It is further noted that the teachings detailed herein are also applicable to other stimulating devices that utilize an electrical current beyond cochlear implants (e.g., auditory brain stimulators, pacemakers, etc.).

The recipient has an outer ear 101, a middle ear 105 and an inner ear 107. Components of outer ear 101, middle ear 105 and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear channel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

As shown, cochlear implant 100 comprises one or more components which are temporarily or permanently implanted in the recipient. Cochlear implant 100 is shown in FIG. 1 with an external device 142, that is part of system 10 (along with cochlear implant 100), which, as described below, is configured to provide power to the cochlear implant, where the implanted cochlear implant includes a battery or other energy storage device (e.g., capacitor) that is charged (e.g., recharged) by the power provided from the external device 142.

In the illustrative arrangement of FIG. 1, external device 142 can comprise a power source (not shown) disposed in a Behind-The-Ear (BTE) unit 126. External device 142 also includes components of a transcutaneous energy transfer link, referred to as an external energy transfer assembly. The transcutaneous energy transfer link is used to transfer power and/or data to cochlear implant 100. Various types of energy transfer, such as infrared (IR), electromagnetic, capacitive and inductive transfer, may be used to transfer the power and/or data from external device 142 to cochlear implant 100. In the illustrative embodiments of FIG. 1, the external energy transfer assembly comprises an external coil 130 that forms part of an inductive radio frequency (RF) communication link. External coil 130 is typically a wire antenna coil comprised of multiple turns of electrically insulated single-strand/or multi-strand platinum or gold wire. External device 142 also includes a magnet (not shown) positioned within the turns of wire of external coil 130. It should be appreciated that the external device shown in FIG. 1 is merely illustrative, and other external devices may be used with embodiments of the present invention.

Cochlear implant 100 comprises an internal energy transfer assembly 132 which can be positioned in a recess of the temporal bone adjacent auricle 110 of the recipient. As detailed below, internal energy transfer assembly 132 is a component of the transcutaneous energy transfer link and receives power and/or data from external device 142. In the illustrative embodiment, the energy transfer link comprises an inductive RF link, and internal energy transfer assembly 132 comprises a primary internal coil 136. Internal coil 136 is typically a wire antenna coil comprised of multiple turns of electrically insulated single-strand/or multi-strand platinum or gold wire.

Cochlear implant 100 further comprises a main implantable component 120 and an elongate electrode assembly 118. In some embodiments, internal energy transfer assembly 132 and main implantable component 120 are hermetically sealed within a biocompatible housing. In some embodiments, main implantable component 120 includes an implantable microphone assembly (not shown) and a sound processing unit (not shown) to convert the sound signals received by the implantable microphone in internal energy transfer assembly 132 to data signals. That said, in some alternative embodiments, the implantable microphone assembly can be located in a separate implantable component (e.g., that has its own housing assembly, etc.) that is in signal communication with the main implantable component 120 (e.g., via leads or the like between the separate implantable component and the main implantable component 120). In at least some embodiments, the teachings detailed herein and/or variations thereof can be utilized with any type of implantable microphone arrangement.

Main implantable component 120 further includes a stimulator unit (also not shown) which generates electrical stimulation signals based on the data signals. The electrical stimulation signals are delivered to the recipient via elongate electrode assembly 118.

Elongate electrode assembly 118 has a proximal end connected to main implantable component 120, and a distal end implanted in cochlea 140. Electrode assembly 118 extends from main implantable component 120 to cochlea 140 through mastoid bone 119. In some embodiments, electrode assembly 118 may be implanted at least in basal region 116, and sometimes further. For example, electrode assembly 118 may extend towards apical end of cochlea 140, referred to as cochlea apex 134. In certain circumstances, electrode assembly 118 may be inserted into cochlea 140 via a cochleostomy 122. In other circumstances, a cochleostomy may be formed through round window 121, oval window 112, the promontory 123 or through an apical turn 147 of cochlea 140.

Electrode assembly 118 comprises a longitudinally aligned and distally extending array 146 of electrodes 148, disposed along a length thereof. As noted, a stimulator unit generates stimulation signals which are applied by electrodes 148 to cochlea 140, thereby stimulating auditory nerve 114.

Because the cochlea is tonotopically mapped (i.e., spatial locations that are responsive to stimulus signals in a particular frequency range are identified), frequencies may be allocated to one or more electrodes of the electrode assembly to generate an electric field in positions in the cochlea that are close to the region that would naturally be stimulated in normal hearing. This enables the prosthetic hearing implant to bypass the hair cells in the cochlea to directly deliver electrical stimulation to auditory nerve fibers, thereby allowing the brain to perceive hearing sensations resembling natural hearing sensations. In achieving this, processing channels of the sound processing unit of the BTE 126 (i.e., specific frequency bands with their associated signal processing paths), are mapped to a set of one or more electrodes to stimulate a desired nerve fiber or nerve region of the cochlea. Such sets of one or more electrodes for use in stimulation are referred to herein as "electrode channels" or "stimulation channels." In at least some exemplary embodiments, each channel has a "base" electrode corresponding to the electrode of the electrode array that is proximate the tonotopically mapped cochlea for a given frequency or frequency range.

Figure 2:
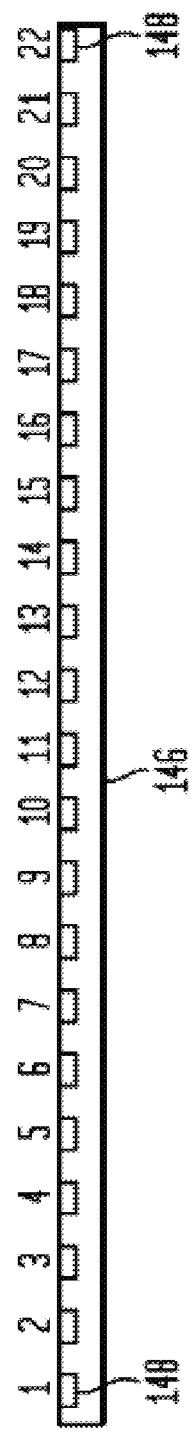
FIG. 2 presents an exemplary electrode array according to an exemplary embodiment.

FIG. 2 illustrates a more detailed view, albeit functionally, of an exemplary electrode array 146 comprising a plurality of electrodes 148 labeled 1-22, in accordance with an embodiment. It is noted that in an exemplary embodiment, the electrode array 146 can have more 12 electrodes, while in other embodiments the electrode array 146 has fewer than 22 electrodes. Indeed, in an exemplary embodiment, the electrode array is a so-called short electrode array that has only 8 or 9 or 10 or 11 or 12 electrodes for example. Briefly, it is noted that with respect to the embodiments that entail evaluating the interaction of respective current spreads with one another for a plurality of electrodes implanted in a recipient, such can entail doing so for at least 6 electrodes, at least 7 electrodes, at least 8 electrodes, at least 9 electrodes, at least 10 electrodes, at least 11 electrodes, at least 12 electrodes, at least 13 electrodes, at least 14 electrodes, at least 15 electrodes, at least 16 electrodes, at least 17 electrodes, at least 18 electrodes, at least 19 electrodes, at least 20 electrodes, at least 21 electrodes, at least 22 electrodes, or more.

In an exemplary embodiment, each electrode 148 is an electrode that corresponds to a specific frequency band channel of the cochlear implant 100, where electrode 22 corresponds to the lowest frequency band (channel), and electrode 1 corresponds to the highest frequency band (channel), as will be discussed in greater detail below. Briefly, it is noted that during stimulation by the electrodes to evoke a hearing percept, one or more electrodes 148 is activated at a given electrode stimulation level (e.g., current level). This electrode stimulation level is pre-set during a fitting process. For example, in at least some instances, an audiologist adjusts stimulation channel electrode current levels of the cochlear implant 100 based on empirical data. More specifically, in at least some embodiments, stimulation channel electrode current levels are adjusted by an audiologist based on threshold and comfort levels. Then, in at least some embodiments, the cochlear implant 100 is configured such that respective stimulation channels of the cochlear implant 100 have those respective current levels. This can be done, for example, by programming the cochlear implant 100 or by any other process that sets the channels of the cochlear implant 100 to have the pertinent electrical stimulation levels. Any arrangement of the cochlear implant 100 and/or other equipment/devices that will enable the teachings detailed herein and/or variations thereof to be practiced can be used in at least some embodiments.

In view of this, an exemplary embodiment entails a fitting method that entails setting or otherwise adjusting the parameters of the cochlear implant 100 determining the electrical mapping from sound levels in one or more or all of the frequency bands to electrical stimulation levels. This exemplary fitting method can include an audiologist or other clinical professional tuning the electrical map parameters of the cochlear implant 100 to the particular auditory physiology of the recipient. That said, as will be described in greater detail below, there can be utilitarian value with respect to disadvantaging (e.g., permanently reducing the output current of the electrode relative to that which would otherwise be the case) or disabling or otherwise not using certain electrodes of the electrode array 146 in a permanent manner (i.e., the result of the mapping/fitting process will result in the configuration of the hearing prosthesis such that one or more of the electrodes are never used or otherwise are disadvantaged according to a specific and predetermined regime, irrespective of the ambient sound captured by the sound capture device of the hearing prosthesis until the prosthesis is refitted or until a new map is selected from a plurality of possible maps or otherwise the electrode disadvantage/disable function is overwritten). Accordingly, an exemplary embodiment entails identifying which of the electrodes of the plurality of electrodes of the electrode array 146 have utilitarian value with respect to the disadvantaging and/or disabling thereof. In an exemplary embodiment, this action of identifying is executed before the action of tuning the electrical map parameters as noted above. Some additional details of this will be described in greater detail below.

It is briefly noted that the teachings detailed herein will typically be described in terms of the permanent disablement of a given electrode. It is noted that this is done for textual economic reasons. In this regard, any disclosure herein with respect to the disablement of an electrode/channel also corresponds to a disclosure of the disadvantaging of an electrode/channel. Corollary to this is that any disclosure with respect to the lack of disablement of an electrode/channel also corresponds to a disclosure of the advantage of an electrode/channel (i.e., permanently increasing the output current of the given electrode relative of to that which would otherwise be the case). Additional details of this are described below.

It is noted that the teachings detailed herein are directed towards a fully functioning implant. That is, there is no defect with respect to the implant. It is entirely up to the recipient and/or the audiologist to determine whether to disable or otherwise disadvantage a given electrode. That is, the electrodes that are disabled or otherwise disadvantaged electrodes are electrodes that could be enabled in otherwise not disadvantaged but for the fact that a determination is made to do so.

Is also noted that actions corresponding to disabling electrodes can be met by enabling a subset of all of the electrodes. That is, the term disabling encompasses both the affirmative act of preventing electrode from operating that otherwise would operate, and the act of omission of not enabling an electrode.

Figure 3:
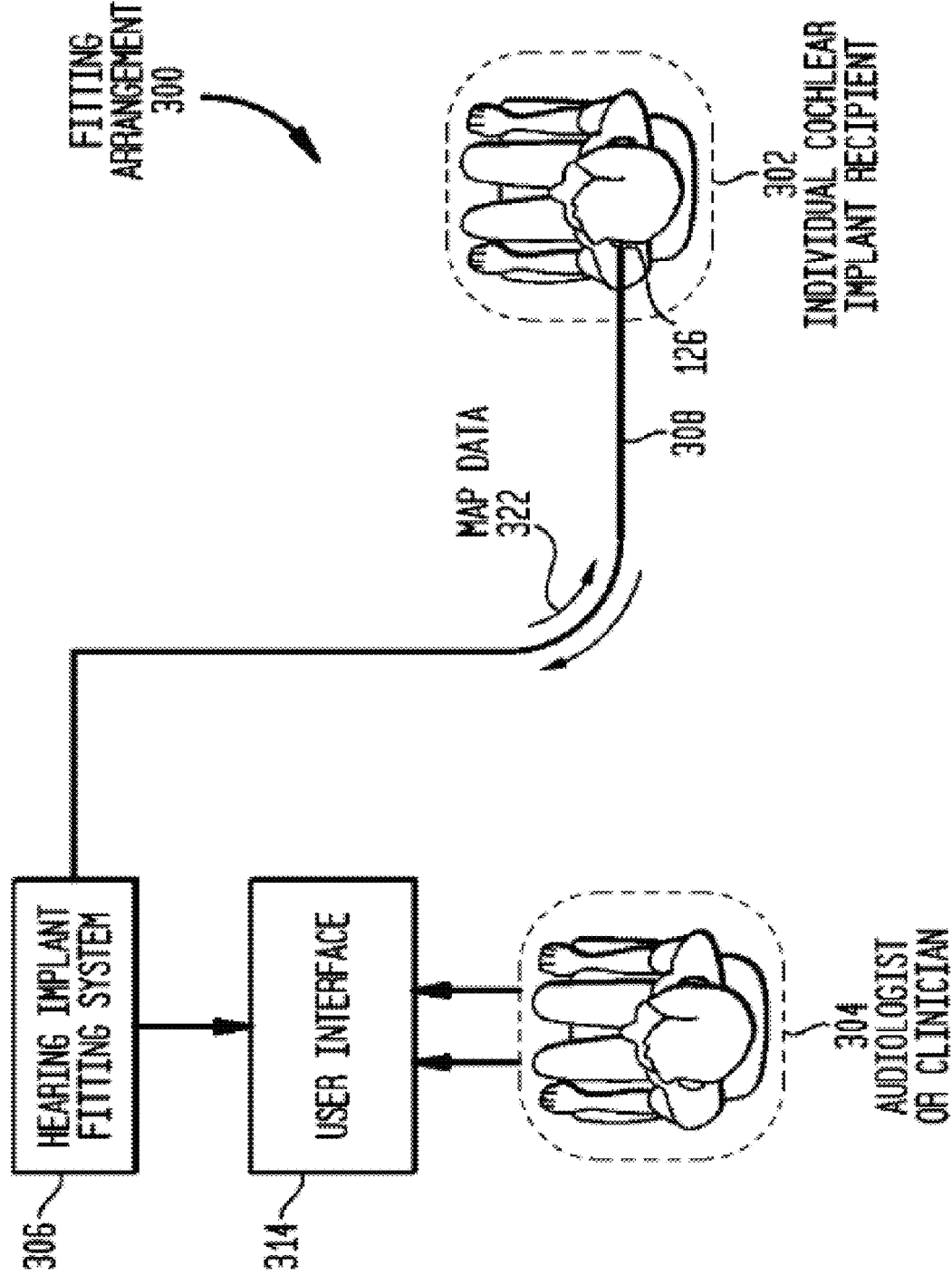
FIG. 3 presents an exemplary device in use according to an exemplary embodiment.

FIG. 3 is a schematic diagram illustrating one exemplary arrangement 300 in which a hearing implant fitting system 306 may be used to fit a cochlear implant in accordance with an embodiment. As shown in FIG. 3, an audiologist or clinician 304 may use a hearing implant fitting system 306 ("fitting system" herein) comprising interactive software and computer hardware to create individualized recipient map data 322 that are digitally stored on system 306, and ultimately downloaded to the memory of the sound processing unit 126 for recipient 302. System 306 may be programmed and/or implement software programmed to carry out one or more of the functions of mapping, neural response measuring, acoustic stimulating, and recording of neural response measurements and other stimuli.

In the embodiment illustrated in FIG. 3, sound processing unit 126 of cochlear implant 100 may be connected directly to fitting system 306 to establish a data communication link 308 between the sound processing unit 126 and fitting system 306. System 306 is thereafter bi-directionally coupled by a data communication link 308 with sound processing unit 126. It should be appreciated that although sound processing unit 126 and fitting system 306 are connected via a cable in FIG. 3, any communications link now or later developed may be utilized to communicably couple the implant and fitting system.

Some exemplary embodiments will now be described in terms of utilizing the aforementioned fitting system 306 to obtain data associated with current spread of respective electrodes and utilize that data to identify which electrodes have utilitarian value with respect to the disablement/disadvantage thereof. It is noted that in some other embodiments, the teachings detailed herein and/or variations thereof can be executed or otherwise implemented utilizing systems other than fitting system 306. Still further, it is noted that any method that will enable the teachings detailed herein and/or variations thereof to be practiced can be utilized in at least some exemplary embodiments. In this regard, it is noted that the following is but exemplary, and that alternative methods can be practiced utilizing other devices other than the fitting system 306 and/or alternative methods can be practiced to implement the teachings herein with respect to a prosthesis that is different than cochlear implant 100.

The following is directed towards an exemplary method that will enable one to gauge or otherwise estimate the power of a given electrode is relative to its neighbors. Corollary to this is that the following is directed towards an exemplary method that will enable one to find the electrodes that stimulate at other areas of the cochlea beyond that which those electrodes are intended to stimulate (i.e., the respective tonotopical stimulation locations). Briefly, the method includes obtaining data with respect to current spread and/or neural spread for a given electrode, and comparing that obtained data to obtained data with respect to current spread and/or neural spread for the neighboring electrodes. As will be understood, the teachings detailed herein are applied in vivo, and are completely subjective to the recipient, although completely objective standards are utilized. That is, the teachings detailed herein are recipient specific.

For the most part, the teachings detailed herein are explained in terms of utilizing current spread functions (electrical spread functions) to based thereon. That said, in alternate embodiments, the teachings detailed herein can be implemented utilizing neural spread functions such as those recorded through an eCAP technique. Some additional details of this alternate manner of implementing the teachings detailed herein are described below. However, it is noted that any disclosure herein with respect to current spread/electrical spread corresponds to disclosure of neural spread in that the same concepts can be utilized to obtain utilitarian value. In this regard, it is noted that the phrase "spread functions" corresponds to the genus that includes only the species of current spread function and the species of neural spread function.

Figure 4:
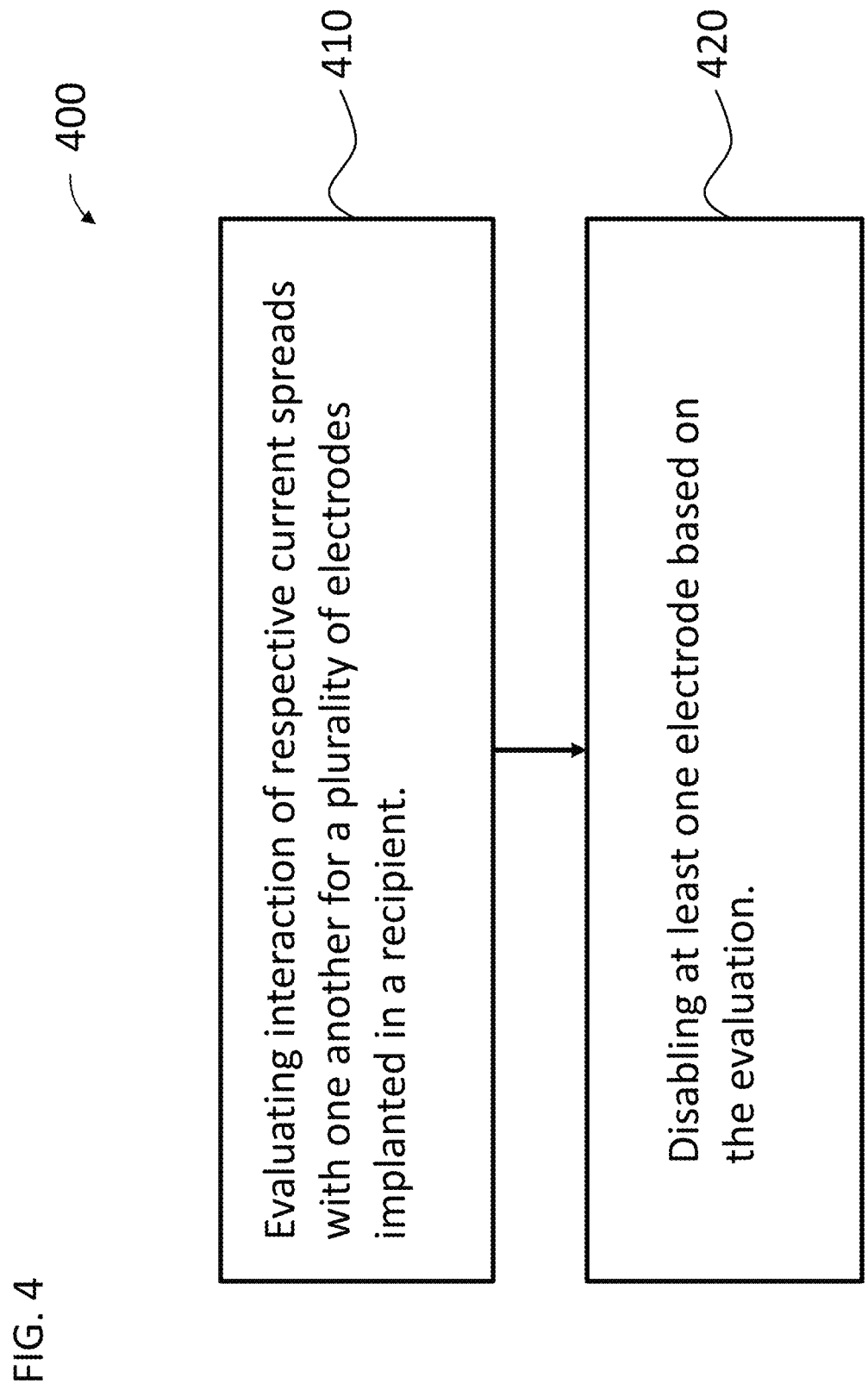
FIG. 4 presents an exemplary flowchart for an exemplary method according to an exemplary embodiment.

More specifically, FIG. 4 presents an exemplary flowchart for an exemplary method, method 400. Method 400 includes method action 410, which entails evaluating interaction of respective current spreads with one another for a plurality of electrodes implanted in a recipient. In an exemplary embodiment, the electrodes correspond to the electrodes 148 of array 146 detailed above. Method 400 further includes method action 420, which entails disabling (or disadvantaging) at least one electrode based on the evaluation. That is, in an exemplary embodiment, the result of method 400 results in an implant where only a subset of the functioning electrodes are utilized or otherwise do enable, where subset refers to a number that is less than the full set. In an exemplary embodiment, this entails creating a map that does not utilize the at least one disabled electrode/purposely permanently avoids energizing that electrode during the utilization of the prosthesis. In an exemplary embodiment, this entails creating a map that disadvantages the electrode/purposely permanently avoids energizing that electrode to that which would otherwise be the case during the utilization of the prosthesis.

Figure 5:
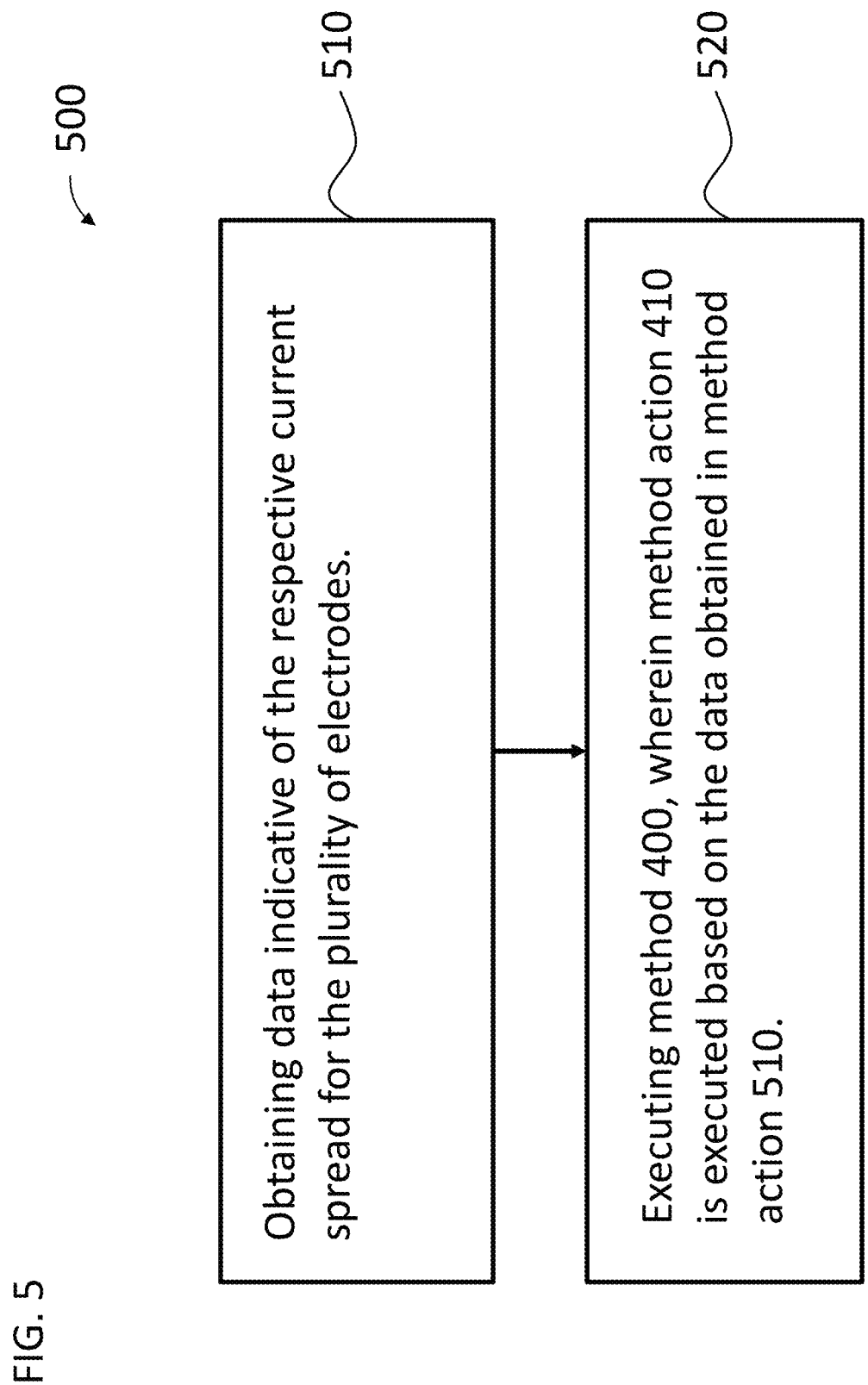
FIG. 5 presents an exemplary flowchart for another exemplary method according to an exemplary embodiment.

It is to be understood that there is utilitarian value with respect to obtaining data indicative of respective current spreads. Indeed, such can be utilized in executing method action 410. In this regard, FIG. 5 presents an exemplary method 500, which includes method 510, which entails obtaining data indicative of respective current spread for the plurality of electrodes. Method 500 further includes method action 520, which entails executing method 400, wherein method action 410 is executed based on the data obtained in method action 510.

Some additional details of method 400 and method 500 will now be described.

With respect to method action 510, in an exemplary embodiment, an audiologist or the like obtains access to a recipient having implanted therein a stimulating device, such as by way of example only and not by way of limitation, a cochlear implant. In an exemplary embodiment, this entails the recipient traveling to a healthcare center or the like. Alternatively, in an exemplary embodiment, method action 510 can be executed remotely. In this regard, in an exemplary embodiment, the healthcare professional can control or otherwise initiate method action 510 remotely, with, for example, the recipient in his or her home. That said, in an alternate embodiment, method action 510 can be executed autonomously by the hearing prosthesis. Some additional details of such are described in greater detail below. It is briefly noted that any method or system or device that can enable method action 510 to be executed can be utilized in at least some exemplary embodiments.

More specifically, method action 510 is executed in one exemplary embodiment by measuring respective spread functions of a plurality of electrodes implanted in the recipient using electrodes of the electrode array 146. In this regard, in an exemplary embodiment, the cochlear implant 100 is configured with Electrode Voltage Telemetry or EVT capabilities or otherwise is configured to enable the measurement of voltages and/or currents at given electrodes. (It is briefly noted that the teachings detailed herein can be accommodated or otherwise adjusted with respect to the utilization of neural spread functions, recorded through evoked Action Compound Potential or eCAP techniques, so as to obtain neural spread functions, as will be described in greater detail below. For now, the present disclosure focuses on measuring current spread of electrodes.) In an exemplary embodiment, method action 510 is executed utilizing an in-vivo EVT measurement in a recipient of cochlear implant 100. In this embodiment, the electrodes of the plurality of electrodes are respectively energized, one at a time, and the intracochlear voltage is measured at the other electrodes. That is, the other electrodes (the non-energized electrodes) are utilized as sense electrodes. In an exemplary embodiment, electrode 1 is energized, and the voltages are measured at the other electrodes (2, 3, 4 . . . 22). Thus, an exemplary embodiment entails obtaining data indicative of respective current spreads for the plurality of first electrodes by applying respective stimulation currents to respective first electrodes in a temporally non-overlapping manner (e.g., electrode 1 without energizing the other electrodes, then electrode 2 without energizing the other electrodes, etc.).

Figure 6:
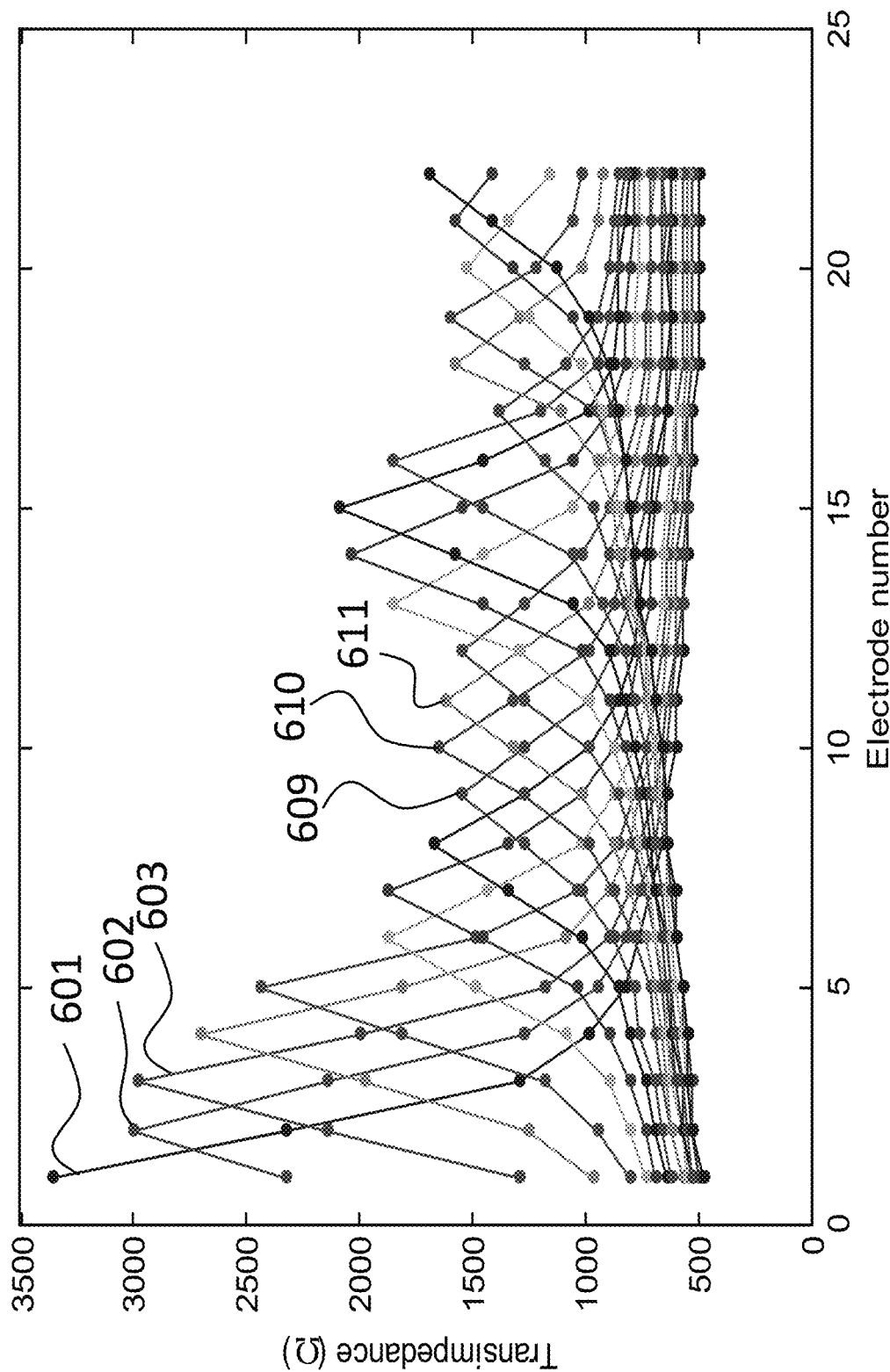
FIG. 6 presents a chart of data obtained according to an exemplary embodiment.

FIG. 6 depicts the exemplary results plotted on a graph for the resulting measurements, where curve 601 corresponds to the resulting measurements associated with energizing electrode 1. In an exemplary embodiment, these exemplary results can be obtained in two or three or five or ten minutes utilizing a cochlear implant that is configured for voltage/current telemetry. As will be briefly described below, in an exemplary embodiment, this can be done automatically by the cochlear implant, while in other embodiments such is executed utilizing the assistance of an audiologist or the like.

The results of FIG. 6 are presented as transimpedance values, where the recorded voltages at the respective recording sites are normalized by the injected current at the stimulation site. Thus, an exemplary embodiment entails obtaining transimpedance at the respective first electrodes while the respective stimulation currents are applied. Next, electrode 2 is energized (in some embodiments, this is done using the same current as that utilized to energize electrode 1, while in other embodiments, the current corresponding to the conform level for that channel/electrode is used, and as will be detailed below, impedance data is scaled by the amount of current delivered, so as to achieve an apples to apples comparison), and the voltages are measured at the other electrodes (1, 3, 4, 5 . . . 22). Curve 602 depicts exemplary results plotted on that graph, superimposed over curve 601. Next, electrode 2 is energized, and the voltages are measured at the other electrodes (1, 2, 4, 5, 6 . . . 22). Curve 603 depicts exemplary results plotted on the graph, superimposed over curve 602 and 601. This goes on for all 22 electrodes. (It is briefly noted that curves 609, 610, and 611 correspond to the measurements associated with energizing electrodes 9, 10, and 11, respectively. These are singled out because additional details of such will be described in greater detail below.) While the embodiment just described details energizing the electrodes in a serial fashion starting with electrode 1, and proceeding to each adjacent electrode, in other embodiments, the electrodes can be energized in a different order (e.g., electrode 1, electrode 22, electrode 2, electrode 21, electrode 3, etc., or electrode 22, 21, 20, 19, etc.). Any order of energizement and voltage measurement can be utilized in some embodiments.

In an exemplary embodiment, the electrodes are energized at comfort levels (C-Levels). That is, in an exemplary embodiment, via a fitting session of the like, the comfort levels for each electrode channel are determined utilizing traditional methods or any other method that can enable such to be determined. Once the comfort levels are determined, the electrodes are energized at those levels (i.e., the voltage and current are applied at levels corresponding to that which would evoke a hearing percept corresponding to the comfort levels for each channel) and the data for FIG. 6 is obtained. In an exemplary embodiment, the electrodes are energized at a percentage X of the comfort levels, while in other embodiments, the electrodes are energized at a percentage Y of the difference between the threshold level (T-Level) and the comfort level for a given channel. In an exemplary embodiment, X and/or Y can be about 50%, about 55%, 60%, 65%, 70%, 75%, 80%, 85%, 90%, 95% or about 100% or any value or range of values therebetween in about 0.1% increments. There is utilitarian value with respect to stimulating each channel at the same percentage X and or Y for that particular channel. Note that this does not mean that the same current is used at each channel. Indeed, just the opposite can be the case, as each channel could have a different comfort level and/or a different threshold level. That said, in some alternate embodiments, the same current is applied to each channel when developing the data associated with FIG. 6. Such same current can be developed based on an understanding of statistical data for a given population (e.g., a given energizemeent will correspond to a hearing percept that is close to a comfort level for a large percentage of a given population). For example, in an exemplary embodiment, a unit value, such as about 160, about 170, about 180 or about 190 units of energizement can be applied to each channel, where the unit value is the same for each channel.

It is briefly noted that the peak values of the spread curves were not actually measured in this embodiment, but instead estimated based on an interpolation technique. In this regard, the cochlear implants intended to develop the data of FIG. 6 are not capable of measuring the intracochlear voltage at the stimulating electrode. This is due to an additional additive contribution, the contact impedance, in the measurement when the electrode is carrying current. That said, in alternate embodiments that can enable such measurement, the measurements at the stimulation site can be taken. Again, any arrangement that can enable the teachings detailed herein can be utilized in at least some exemplary embodiments, and if such can enable the measurement of the current or voltage at the energized electrode in an accurate or otherwise utilitarian matter, such can be done.

As can be seen from FIG. 6, there is clearly overlap between the curves. In the exemplary embodiment seen in FIG. 6, some of the more remote electrodes are almost as effective in generating a given voltage at a given site as the closer electrodes, all other things being equal. In at least some instances, this overlap will mask the content of other channels.

Again, it is noted that the values of FIG. 6 have been presented in terms of transimpedance values (ohms). In other embodiments, other values can be utilized, such as that seen in FIG. 7, which depicts the voltage measurements for electrodes 9, 10, and 11. In this regard, curves 709, 710, and 711, correspond to the measurements for electrodes 9, 10, and 11 respectively. Curves 709, 710, and 711 correspond to curves 609, 610, and 611, except in terms of voltage instead of impedance/transimpedance. The data associated with FIG. 7 will be discussed in more detail below. However, FIG. 7 depicts a relatively less crowded graph so that the physical phenomenon associated with the concepts presented herein can be more easily seen.

Thus, in an exemplary embodiment, there is an action of applying respective stimulation currents to respective electrodes in a temporally nonoverlapping manner, and obtaining data indicative of transimpedance at respective electrodes while the respective stimulation currents are applied. In an exemplary embodiment, the data indicative of transimpedance is pure transimpedance data (e.g., 2350 kOhms for curve 601 at electrode 2), while in other embodiments, the data indicative of transimpedance is in voltage levels (which can be converted to ohm values).

Figure 7:
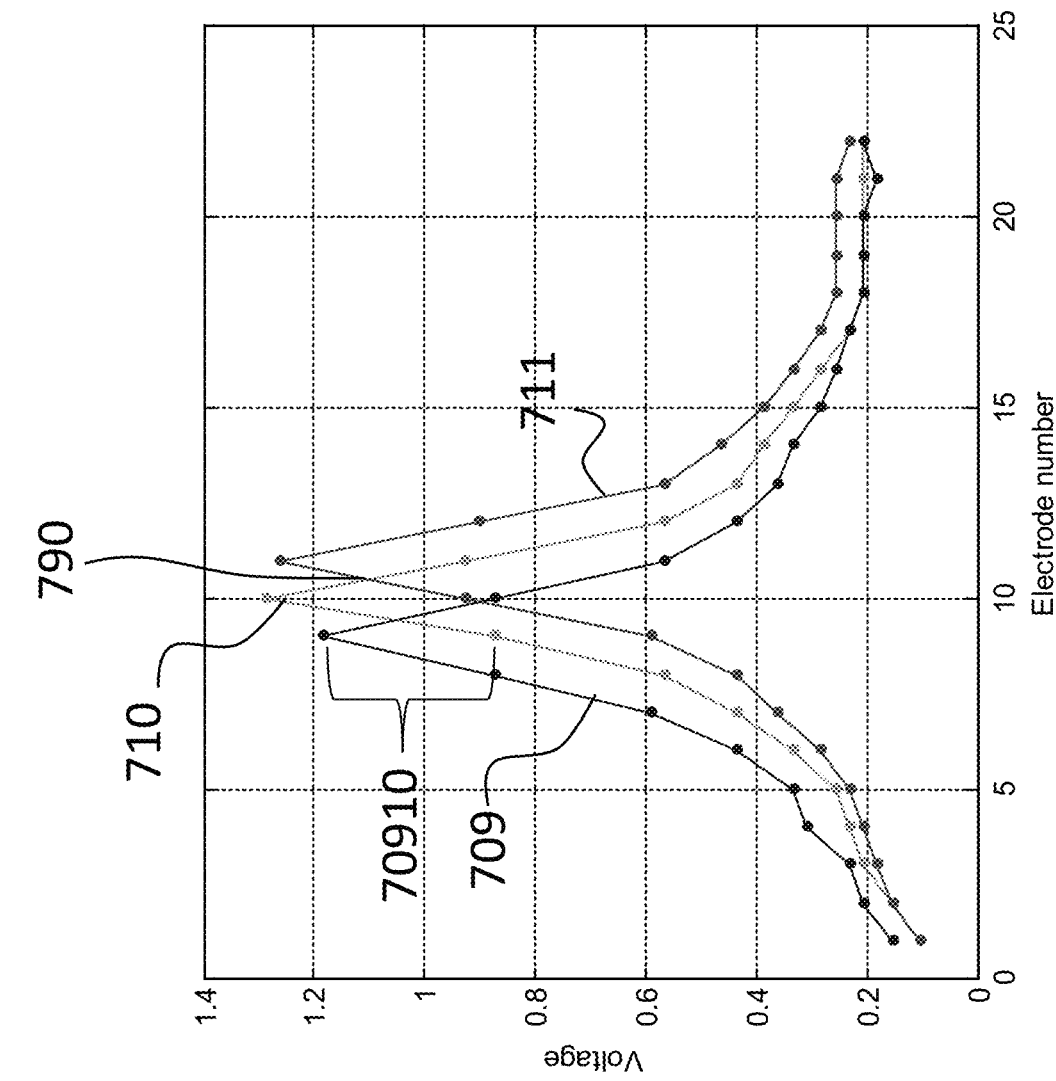
FIG. 7 presents another chart of data obtained according to an exemplary embodiment.

It is also noted that the data presented in FIG. 7 is data that was subject to a preprocessing action corresponding to the subtraction of the minimum voltage value, thus shifting the curves toward zero. With reference to the embodiment of FIG. 6, this would entail reducing all of the values therein by about 500 ohms, as that is the resistance that is left over after the current leaves the cochlea. That is, irrespective of the electrode at issue, there is always an amount of resistance left over after the current leaves the cochlea. In this regard, there can be utilitarian value with respect to narrowing or otherwise limiting the data to that directed to the part of the current or voltage that drives the auditory nerve (e.g., the area 810 of FIG. 8 discussed below), as opposed to the current or voltage that is associated with the extra cochlear tissue (the area below the area 810 of FIG. 8). In an exemplary embodiment, this voltage can be estimated or otherwise assumed. This can have the effect of reducing or otherwise eliminating the effects of the inherent impedance in tissue in the evaluation. More particularly, the raw voltages, if plotted (or raw impedance measures with respect to FIG. 6, which have not been adjusted), include a variable part and also a large offset (0.5 kOhms with respect to FIG. 6) shared by all the curves and thus all the electrode positions. That is, this part of the voltage measured is common to all electrodes. In at least some exemplary embodiments, this can reflect the electrical resistance for the current to flow from anywhere in the cochlea to the reference electrode. Thus, in at least some exemplary embodiments, this contribution can be disregarded or otherwise discounted in that in at least some exemplary embodiments, this contribution is not effective in generating local action potentials. Such disregarding of the offset can result in the data used to compare the electrode under consideration with its neighboring electrodes being more sensitive to the underlying variable part, and thus less biased.

Thus in view of the above, obtaining the data corresponding to FIGS. 7 and 6 can correspond to the data resulting from method action 510 of method 500. It is briefly noted that the action of obtaining data indicative of the respective current spread for the plurality of electrodes can be executed by obtaining the results of the stimulation and measurement as opposed to taking the actual measurements. In this regard, method action 510 can be executed by receiving a data package or the like from a remote cochlear implant containing data indicative of the respective current spreads. That is, it is not necessary to actually execute the electrode energizement and take the actual measurements. This action can be done by another actor.

After obtaining the data indicative of the respective current spread for the plurality of electrodes (by, for example, using the non-energized electrodes of the electrode array 146, or by the eCAP techniques that will be described in greater detail below), the data indicative of the respective current spread is analyzed or otherwise evaluated. The following presents but one exemplary embodiment of an evaluation of the data indicative of the respective current spreads. It is noted that alternate embodiments can be practiced utilizing other manners of evaluation, some of which are described below. Any device, system, or method that will enable the evaluation of the interaction of respective current spreads with one another that can enable the teachings detailed herein can be utilized in at least some exemplary embodiments.

With respect to an exemplary embodiment of evaluating the interaction of respective current spreads, an electrode impedance factor, which reflects the independence of a given electrode from its neighboring electrodes, is developed for each electrode. As used herein, the phrase "neighboring electrodes" corresponds to the electrode closest to the given electrode on one side and the electrode closest to the given electrode one the opposite side. For example, with respect to electrode 9, the two neighboring electrodes are electrode 8 and electrode 10. This is distinguished from, for example, proximate electrodes, which could also include electrodes 7 and 11 in addition to the neighboring electrodes, or others potentially. Indeed, while the embodiments described below will be described with emphasis on establishing the independence associated with the neighboring electrodes, other embodiments can be utilized where the independence associated with the other proximate electrodes is evaluated. In this regard, in an exemplary embodiment, current spread evaluation can be executed by evaluating the current spread of a given electrode of interest and the current spreads which result from the electrodes that are 1, 2, 3, 4, 5, 6, 7, 8, 9, 10, 11, and/or 12 electrodes away from the given electrode of interest in one or more directions (e.g., 5 electrodes on the basal side of electrode 10 (electrodes 9, 8, 7, 6 and 5) and 3 electrodes on the apical side of electrode 10 (electrodes 11, 12 and 13). Still, as will be understood, in such embodiments, the action of evaluating interaction of respective current spreads with one another for a plurality of electrodes implanted in a recipient entails evaluating interaction of current from at least two electrodes with respective electrodes of a plurality of electrodes (e.g., the neighboring electrodes) and not evaluating interaction of current from at least one other electrode with the respective electrodes of the plurality of electrodes (e.g., one of the neighbors of the neighboring electrodes).

Still, with respect to the embodiment under discussion, the evaluation is directed towards determining to what extent the given electrode can stimulate neural tissue in a significantly different way from the other electrodes, or at least the "neighboring electrodes." This is achieved by comparing respective stimulation fields of electrodes with respective stimulation fields of neighboring electrodes. In the following exemplary embodiment, which is by way of example only and not by way of limitation, an evaluation is made of the current spread for the electrode under consideration and dominating current spreads for the neighboring electrodes. By "dominating current spreads," it is meant the portion of the current received/present at a given location that is greater than that which corresponds to the current at the given location resulting from stimulation of the given electrode. With reference to FIG. 7, where the electrode under consideration is electrode 10 (the electrode where the independence thereof is being quantified), the dominating current spread is conceptually represented by 70910, which is the difference between the voltage of electrode 9 when energized at that location, and the voltage measured at that location when electrode 10 is energized (and electrode numeral 9 is not energized—or any other electrode is energized). Here, the difference 70910 is the difference between 1.1851 volts (the voltage that is present at electrode 9 when energized) and 0.8759 volts (the voltage that is present at electrode 9 when electrode 10 is energized). (Additional specifics of the data are discussed below.) It is briefly noted that in the exemplary embodiment presented in FIG. 7, the voltages are voltages for the same current applied to each electrode. That said, in an alternate embodiment, the voltages can be normalized with respect to different input (energizement) voltages.

More specifically, continuing under the scenario where it is attempted to quantify the independence of electrode 10, the stimulation field of electrode 10 is compared to the stimulation field that results from energizement of the neighboring electrodes by a comparison of the overall stimulation field for electrode 10 with the dominating voltage. In this exemplary embodiment, the following numerical calculations can be utilized to achieve such comparison. Basically, the area under the curve (curve 710) associated with the energizement of electrode 10 is compared to the area above that curve and below the curves associated with the energizement of electrodes 9 and 11 (the neighboring electrodes)—curves 709 and 711. The area below curve 710 is represented by the shaded portion 810 (the portion having the hatching with no slope). The area above the curve 710 and below curve 709 is represented by the shaded portion 809 (the portion with the hatching having the negative slope). The area above the curve 710 and below curve 711 is represented by the shaded portion 811 (the portion with the hatching having the positive slope). The areas 809 and 811 correspond to the areas where the expectation of the neighboring electrodes is exceeding that of the electrode under consideration (electrode 10). Areas 809 and 811 are indicative of the neighboring electrodes generating a larger voltage than that of the electrode under consideration, and are therefore more effective at driving neurons at those locations than the electrode under consideration. Because the teachings detailed herein address the interactive effects of the electrode under consideration and the neighboring electrodes with respective current spread, electrode impedance factors are developed based on the interactive effects. Below is represented in the exemplary method/equation for developing electrode impedance factors that take into account the effects of current spread with respect to the electrode under consideration and the neighbors thereof. It is noted that this is but one exemplary method/equation for developing electrode impedance factors. Any method or system that will develop electrode impedance factors that can have utilitarian value with respect to determining which electrodes to disable can be utilized in at least some exemplary embodiments.

The following equation can be utilized in an exemplary embodiment so as to quantify the independence of the electrode 10:

$$((\int Cbas709 - \int Cbas710) + (\int Capic711 - \int Capic710))/(\int C710) = \text{Weight for Electrode 10} \quad (1)$$

where:

$\int Cbas709$ is the area under curve 709 on the basal side of electrode 709;

$\int Cbas710$ is the area under curve 710 on the basal side of electrode 709

$\int Capic711$ is the area under curve 711 on the apical side of electrode 711;

$\int Capic710$ is the area under curve 710 on the apical side of electrode 711; and $\int C710$ is the area under curve 710.

In view of the above, it can be seen that $\int Cbas709 - \int Cbas710$ corresponds to the dominating current spread of neighboring electrode 9 because that is the difference between the two curves (709 and 710) and $\int Capic711 - \int Capic710$ corresponds to the dominating current spreads of neighboring electrode 11 because that is the difference between the two curves (711 and 710).

The following table presents exemplary recorded voltages at respective given electrodes (electrodes 1 to 22) for the energizement of electrode 9, electrode 10, and electrode 11 in a temporally separate manner (i.e., no two electrodes are energized at the same time), with the caveat that the recorded voltage for the electrode that is energized is estimated for reasons detailed above.

| Recorded Voltage at Electrode # | Electrode 9 Energized | Electrode 10 Energized | Electrode 11 Energized |
| --- | --- | --- | --- |
| REC01 | 0.1546 | 0.103  | 0.103  |
| REC02 | 0.2061 | 0.1546 | 0.1546 |
| REC03 | 0.2319 | 0.2061 | 0.1803 |
| REC04 | 0.3091 | 0.2319 | 0.2061 |
| REC05 | 0.3349 | 0.2576 | 0.2319 |
| REC06 | 0.438  | 0.3349 | 0.2834 |
| REC07 | 0.5925 | 0.438  | 0.3607 |
| REC08 | 0.8759 | 0.5668 | 0.438  |
| REC09 | 1.1851 | 0.8759 | 0.5925 |
| REC10 | 0.8759 | 1.2881 | 0.9274 |
| REC11 | 0.5668 | 0.9274 | 1.2624 |
| REC12 | 0.438  | 0.5668 | 0.9017 |
| REC13 | 0.3607 | 0.438  | 0.5668 |
| REC14 | 0.3349 | 0.3864 | 0.4637 |
| REC15 | 0.2834 | 0.3349 | 0.3864 |
| REC16 | 0.2576 | 0.2834 | 0.3349 |
| REC17 | 0.2319 | 0.2319 | 0.2834 |
| REC18 | 0.2061 | 0.2061 | 0.2576 |
| REC19 | 0.2061 | 0.2061 | 0.2576 |
| REC20 | 0.2061 | 0.2061 | 0.2576 |
| REC21 | 0.1803 | 0.2061 | 0.2576 |
| REC22 | 0.2061 | 0.2061 | 0.2319 |

Figure 8:
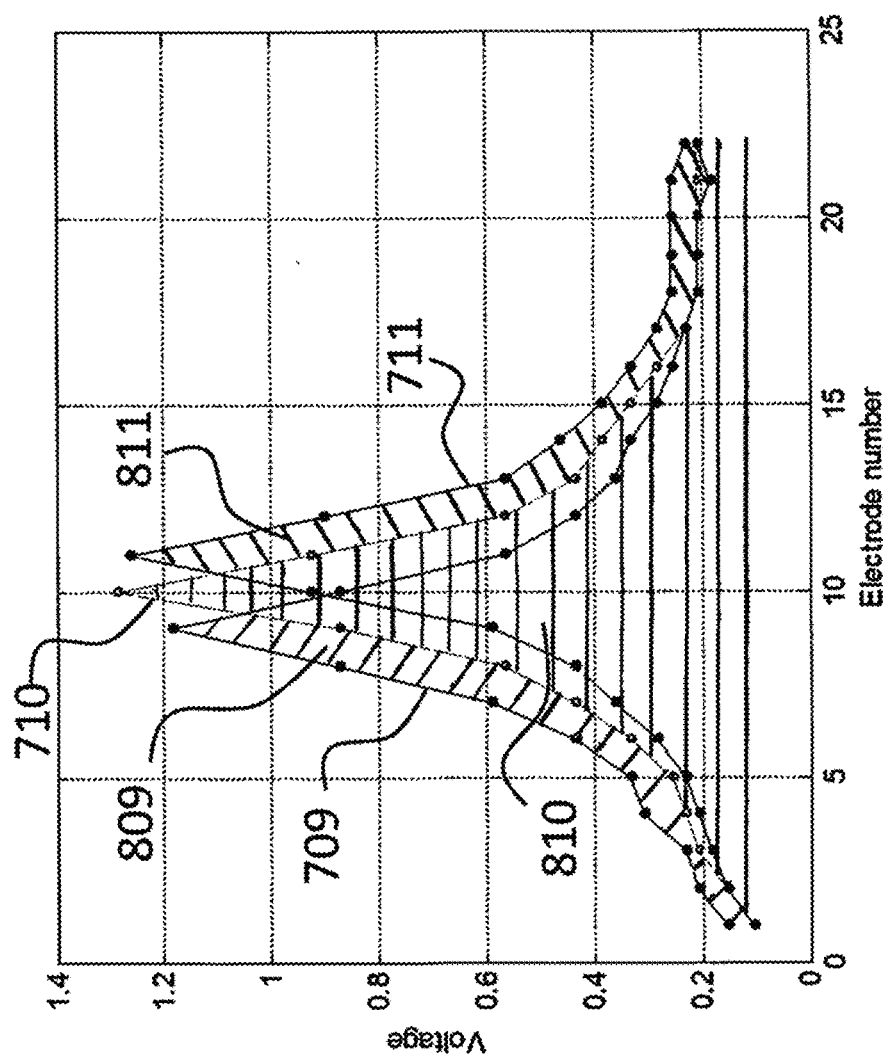
FIG. 8 presents a reproduction of the chart of FIG. 7 in an annotated fashion.

The data of the above table corresponds to the charted data in FIGS. 7 and 8. With respect to equation (1), $\int C710$, the integral of curve 710 (i.e., the area below curve 710), corresponds to 8.6562 volts (the summation of column "Electrode 10 Energized"). Accordingly, the integral of curve 710 can be obtained utilizing numerical analysis methods. Alternatively, an equation can be developed for the curve 710, and a proper integral can be obtained for that equation. Any device, system, or method that will enable the area under the curve 710 to be calculated can be utilized in at least some exemplary embodiments.

Still with respect to equation (1), $\int Cbas709 - \int Cbas710$, the integral of curve 709 minus curve 710 with respect to the basal side thereof (i.e., the side encompassing electrodes 1-9, the electrodes closest to the round or oval window, etc.) is calculated, which corresponds to 1.1593 volts. This corresponds to the dominating current spread resulting from the energizement of electrode 9. In this exemplary embodiment, the reason why the resulting voltages associated with the electrodes on the apical side of electrode 9 are not considered is because none of these voltages represent a dominating current spread relative to electrode 10. If there was a voltage recorded that was higher than the voltage recorded with respect to the energizement of electrode 10 at an electrode that was apical to electrode 9, in at least some exemplary embodiments that could be included in the calculation of the dominating spread associated with electrode 9, and thus equation (1) would instead be:

$$((\int Cdominat709 - \int Cdominated710) + (\int Cdominant711 - \int Cdominated710))/(\int C710) = \text{Weight for Electrode } 10 \quad (2)$$

where:

∫Cdominant709 is the area under curve 709 wherever curve 709 is above curve 710 (i.e., electrode 9 dominates electrode 10);

∫Cdominated710 is the area under curve 710 wherever curve 709 is above curve 710 (i.e., electrode 9 dominates electrode 10);

∫Cdominant711 is the area under curve 711 wherever curve 711 is above curve 710 (i.e., electrode 11 dominates electrode 10);

∫Cdominated710 is the area under curve 710 wherever curve 711 is above curve 710 (i.e., electrode 11 dominates electrode 10); and ∫C710 is the area under curve 710.

With respect to equation (1), for convenience, it is presumed that no location on the apical side of electrode 10 will experience a scenario where the electrode current spread from electrode 9 would dominate the spread from electrode 10, and vice versa for the basal side of electrode 10 with respect to electrode 11. Equation (2) thus presents a more accurate equation in some embodiments, as it takes into account the possibility that there could be dominating current spreads on the opposite sides of the electrode of interest.

Still with respect to equation (1), ∫Capic711−∫Capic710, the integral of curve 711 minus curve 710 with respect to the apical side thereof (i.e., the side encompassing electrodes 11 to 22 the electrodes furthest from the round or oval window, etc.) is calculated, which corresponds to 1.2624 volts. This corresponds to the dominating current spread resulting from the energizement of electrode 11.

Thus, the result of equation (1) is 0.2797, which is the weight for electrode 10. In percentage terms, this would correspond to 27.97% (i.e., if the results of all of the integrals were multiplied by 100). Accordingly, in an exemplary embodiment, the impedance factor for electrode 10 is 27.97%.

In an exemplary embodiment of method action 410, the above calculations are repeated for each of the electrodes. Accordingly, equation 1 can be rewritten as follows:

$$((\int CbasE\#-1 - \int CbasE\#) + (\int CapicE\#+1 - \int CapicE\#))/(\int CE\#) = \text{Weight for Electrode } E\# \quad (3)$$

where:

E# is the electrode of interest,

E#−1 is the basal neighbor of the electrode of interest;

E#+1 is the apical neighbor of the electrode of interest;

∫CbasE#−1 is the area under the curve for electrode E#−1 on the basal side of E#−1;

∫CbasE# is the area under the curve for E# on the basal side of electrode E#−1;

∫CapicE+1 is the area under curve for electrode E#+1 on the apical side of electrode E#+1;

∫CapicE# is the area under curve for E# on the apical side of electrode E#+1; and ∫CE# is the area under the curve for electrode E#.

Equation (3) represents an exemplary equation utilizing spread data to develop electrode impedance factors for respective electrodes.

It will be understood from the above equations that the equations are electrode-of-interest centric in that the above equations do not take into account the fact that there is a space between the electrode of interest and the neighboring electrodes which is dominated by the electrodes spread of the neighboring electrode. This is represented by way of example in FIG. 7 at point 790 with respect to curves 711 and 710. In this regard, the above equations assume that point 790 is in fact located at a position just before the apex of curve 711. This is done for purposes of convenience and for purposes of ease of illustration of the concept detailed herein. It is to be understood that in an exemplary embodiment, the above equations can be modified to take into account the fact that current spread from the neighboring electrodes dominates the electrode under consideration at a location closer there to (e.g., at point 790 instead of just before the apex of curve 711). Again, the evaluative methods detailed herein are but examples. Any method or regime of the evaluation that can have utilitarian value can be utilized in at least some exemplary embodiments.

For example, as noted above, instead of limiting the interactions to the neighboring electrodes, the effects of current spread of the neighbors of the neighboring electrodes can also be included into the equations. Still further, instead of addressing only the dominant portion of the current spreads, the entire portion of the current spread can be addressed. Such an equation could be:

$$(\int CbasE\#-1 + \int CapicE\#+1)/(\int CE\# = \text{Weight for Electrode } E\# \quad (4)$$

where:

E# is the electrode of interest,

E#−1 is the basal neighbor of the electrode of interest;

E#+1 is the apical neighbor of the electrode of interest;

∫CbasE#−1 is the area under the curve for electrode E#−1 on the basal side of E#−1;

∫CapicE+1 is the area under curve for electrode E#+1 on the apical side of electrode E#+1; and ∫CE# is the area under the curve for electrode E#.

Another equation could be, which takes into account the neighboring electrodes of the neighboring electrodes:

$$((\int CbasE\#-2 - \int CbasE\#-1) + (\int CbasE\#-1 - \int CbasE\#) + (\int CapicE\#+1 - \int CapicE\#) + (\int CapicE\#+2 - \int CapicE\#+1))/(\int CE\#) = \text{Weight for Electrode } E\# \quad (5)$$

where:

E# is the electrode of interest,

E#−1 is the basal neighbor of the electrode of interest;

E#−2 is the basal neighbor of basal neighbor the electrode of interest;

E#+1 is the apical neighbor of the electrode of interest;

E#+2 is the apical neighbor of the apical neighbor of the electrode of interest;

∫CbasE#−1 is the area under the curve for electrode E#−1 on the basal side of E#−1;

∫CbasE#−2 is the area under the curve for electrode E#−2 on the basal side of E#−2;

∫CbasE# is the area under the curve for E# on the basal side of electrode E#−1;

∫CapicE+1 is the area under curve for electrode E#+1 on the apical side of electrode E#+1;

∫CapicE+2 is the area under curve for electrode E#+2 on the apical side of electrode E#+2;

∫CapicE# is the area under curve for E# on the apical side of electrode E#+1; and ∫CE# is the area under the curve for electrode E#.

Alternatively, the spreading functions can be truncated after two electrodes or three electrodes, etc., from the main electrode (e.g., the effects of the neighboring electrode current spread are halted at the location of electrodes 7 and 13), as the effects of neighboring electrode current spread beyond that point could be considered to be subsumed by current spread from other electrodes. Any system or method that can develop an impedance factor or otherwise winning functions that addresses the phenomenon of current spread can be utilized in at least some exemplary embodiments.

Another way to calculate weighting or an impedance factor could be to calculate the signal to interference ratio defined as the voltage at the electrode under consideration divided by the average voltage at the same site when other electrodes are stimulating. Indeed, a combination of this and equation (3) can be utilized, where the average result is used.

Another way to calculate weighting or an impedance factor could be to compare the widths of area 810 to areas 809 and 811 at a given voltage location for a given electrode. Again, any value having utilitarian with respect to weighting or otherwise determining electrode impedance factor can be utilized in at least some exemplary embodiments.

Figure 9:
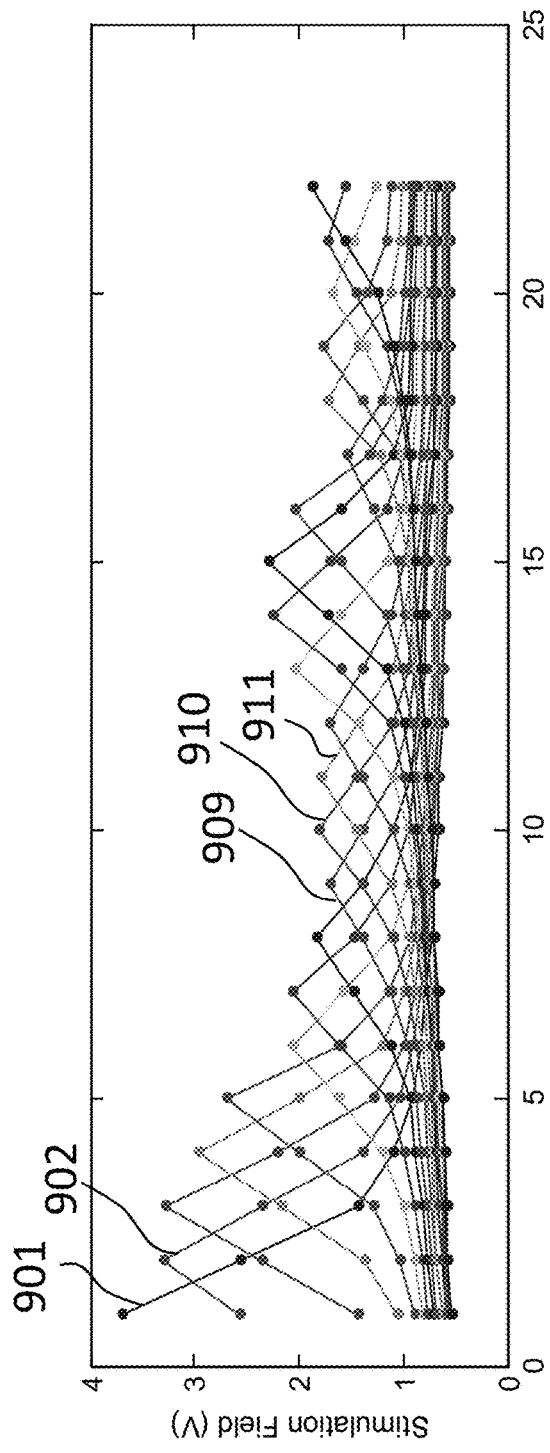
FIG. 9 presents a chart of data obtained according to an exemplary embodiment.

As noted above, embodiments can be utilized with respect to evaluating the data based on the transimpedance or voltage, or any other value that can have utilitarian value. Moreover, as noted above, some embodiments are practiced by canceling out the offsets shared by all the electrode position, while other embodiments are practiced without such canceling. While the embodiment of FIG. 7 is presented with such canceling, FIG. 9 presents a full stimulation field spread for each electrode without cancellation. In this regard, curve 901 corresponds to the result of method action 510 vis-à-vis electrode 1, curve 902 corresponds to the result of method action 510 vis-à-vis electrode 2, and so on, where curves 909, 910, and 911 correspond to the result of method action 510 for electrodes 9, 10, and 11 respectively.

Figure 10:
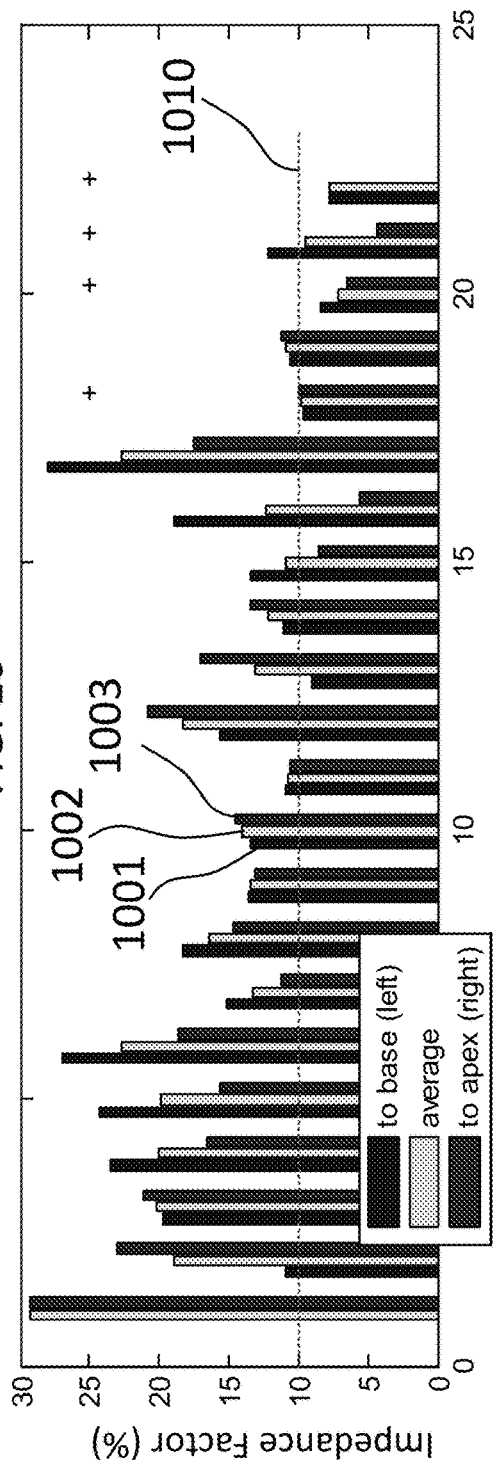
FIG. 10 presents a chart of an analysis of the data of FIG. 9.

Again, as noted above, in an exemplary embodiment of method action 410, the above calculations are repeated for each of the electrodes. FIG. 10 presents in graphical terms the results of such repeated calculations with respect to the data field presented in FIG. 9. With respect to electrode 10, it can be seen that there exists three bars, bars 1001, 1002, and 1003. These bars respectively represent the basal portion of the current spreads of electrode 9 and 10 (i.e., the results of ($fCbas709-fCbas710$)/($fC710$), the average of the basal and apical portion of the current spreads of electrodes 9, 10 and 11 (i.e., equation (1)), and the apical portion of the dominating current spreads of electrode 10 and 11 (i.e., ($fCapic711-fCapic710$))/($fC710$)). The basal and apical bars 1001 and 1003 presented for visual purposes to illustrate how in some instances, there can be a significant difference between the two, while in other instances, the two are relatively indifferent. Also, the basal and apical bars are presented so as to illustrate the fact that with respect to the basal most electrode, electrode 1, there will be no basal portion of current spread, because there are no electrodes located on the basal side thereof. Corollary to this is that with respect to the apical most electrode, electrode 22, there will be no apical portion of current spread, because there are no electrodes located on the apical side thereof. Thus, FIG. 10 presents for electrode 1 a bar for the average, and a bar for the apical spread which are the same. Also, FIG. 10 presents for electrode 22 a bar for the average, and a bar for the basal spread which are the same.

Still with respect to FIG. 10, for the purposes of this embodiment, the average values (e.g., results of equation (1), or more appropriately, as FIG. 10 is addressing all electrodes, the results of equation (3)) are utilized as the impedance factors for each electrode. Thus, in an exemplary embodiment, there is a method which determines which electrodes of the prosthesis to disable based on current spread within a recipient by weighting respective electrodes by dividing summation of values based on dominating current spreads generated by neighboring electrodes of a respective value by a value based on a current spread for the respective electrode.

With respect to FIG. 10, it can be seen that electrode 20 has the lowest impedance factor. Thus, based on the calculations above, electrode 20 can be considered to be the electrode with the largest overlap and thus the worst electrode in conveying information crisply to the auditory nerve. Thus, electrode 20 represents the best candidate to disable (or deemphasize—the current embodiment is directed towards identifying electrodes for disablement, but alternate embodiments can be directed towards the emphasis of the electrode/channel—more on this below). Accordingly, with respect to method action 420, electrode 20 would be deactivated. With respect to the method of determining which electrodes of the prosthesis to disable based on current spread within a recipient by weighting respective electrodes by dividing summation of values based on dominating current spreads generated by neighboring electrodes of a respective value by a value based on a current spread for the respective electrode, the electrode that is disabled is the electrode associated with the lowest result of that division.

Figure 11:
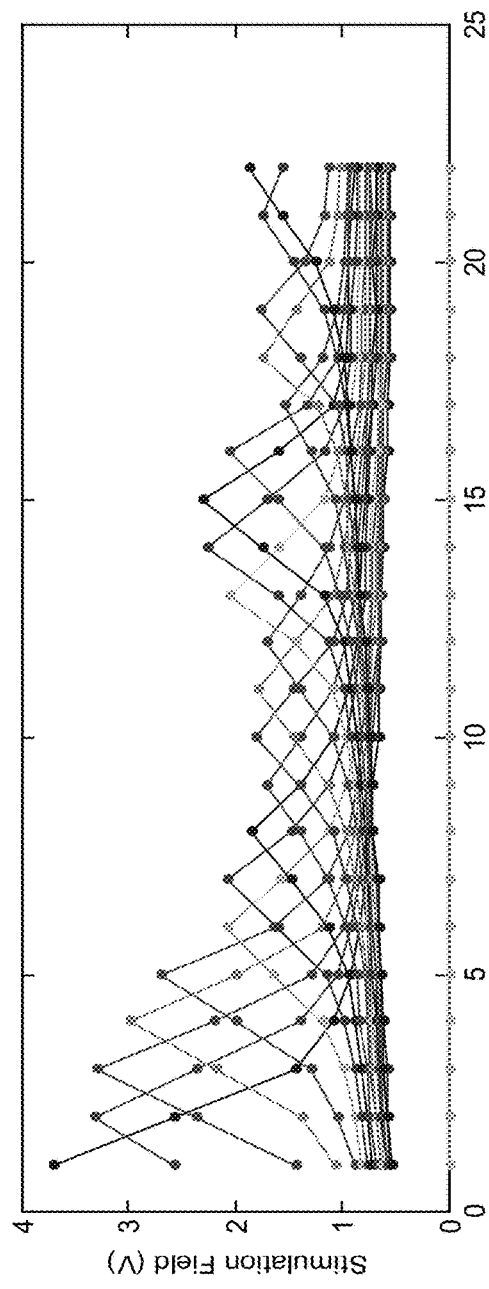
FIG. 11 presents a chart of data obtained according to an exemplary embodiment.
Figure 12:
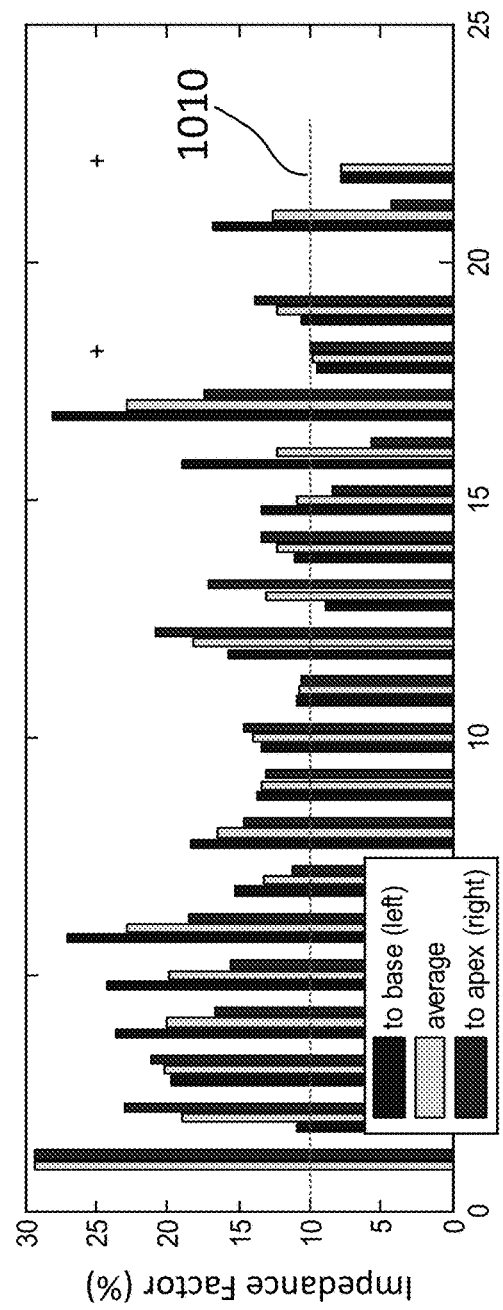
FIG. 12 presents a chart of an analysis of the data of FIG. 10.

However, there is utilitarian value with respect to deemphasizing or otherwise disabling more than one electrode. In an exemplary embodiment, a criterion can be established whereby electrodes that have an impedance value lowest certain threshold will be disabled, and electrodes above the threshold level will not be disabled. In the embodiment represented in FIG. 10, this threshold level is presented as an impedance factor of 10%, and is graphically illustrated by line 1010. In an exemplary embodiment, this predetermined threshold can be developed based on empirical and/or statistical data for a given population. In an exemplary embodiment, the threshold can be applicable to a given recipient having a given human factors profile. For example, some thresholds can be found to be statistically utilitarian for a population of humans having at least a high school education between ages 18 and 36, and other thresholds can be found to be statistically utilitarian for a population of humans who can read between the ages of 8 and 16. Still further, other thresholds can be statistically utilitarian for population of humans that are above age 65, etc. Any threshold that can have utilitarian value can be utilized in at least some exemplary embodiments. Here, the threshold has been determined by way of example only and not by way of limitation, as 10%. Accordingly, in an exemplary embodiment, the electrodes indicated by the "+" sign on FIG. 10 would be deactivated (electrodes 18, 20, 21, and 22). However, in view of the fact that the various current spreads are not only a factor of a given electrode under consideration, but are also a factor of other electrodes, an iterative process is utilized where, for example, the electrode with the lowest impedance factor is disabled, and then method action 510 is reexecuted for all electrodes, but with electrode 20 disabled. FIG. 11 represents the results of such method action in graphical terms. Then, the results are reevaluated, where FIG. 12 represents, again in graphical terms, the results of such reevaluation. As can be seen, electrodes 18 and 22 have average impedance factors below the threshold set at 10%. However, as can be seen, electrode 21 has an average impedance factor of above the threshold. Thus, disabling electrode 20 results in an improvement in the utilitarian value of electrode 21.

Figure 13:
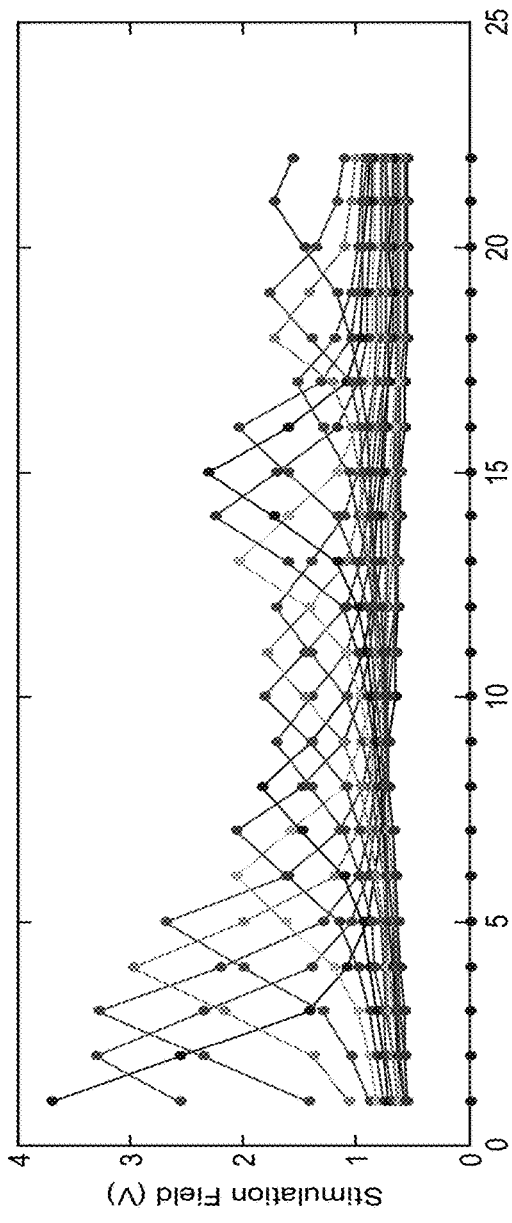
FIG. 13 presents a chart of data obtained according to an exemplary embodiment.
Figure 14:
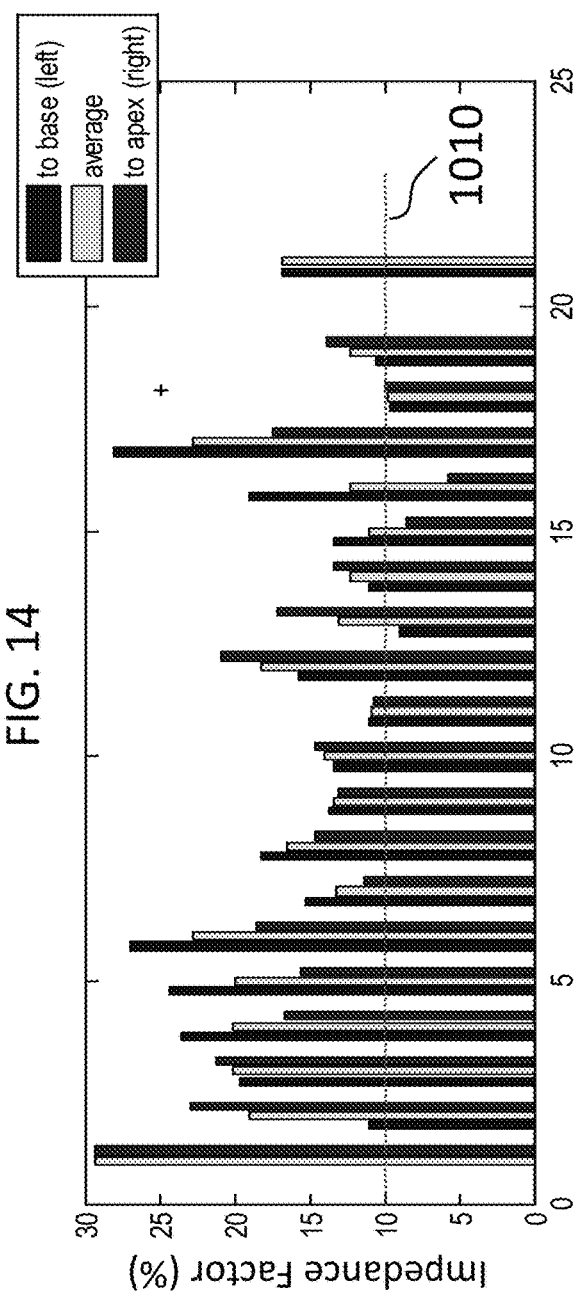
FIG. 14 presents a chart of an analysis of the data of FIG. 13.
Figure 15:
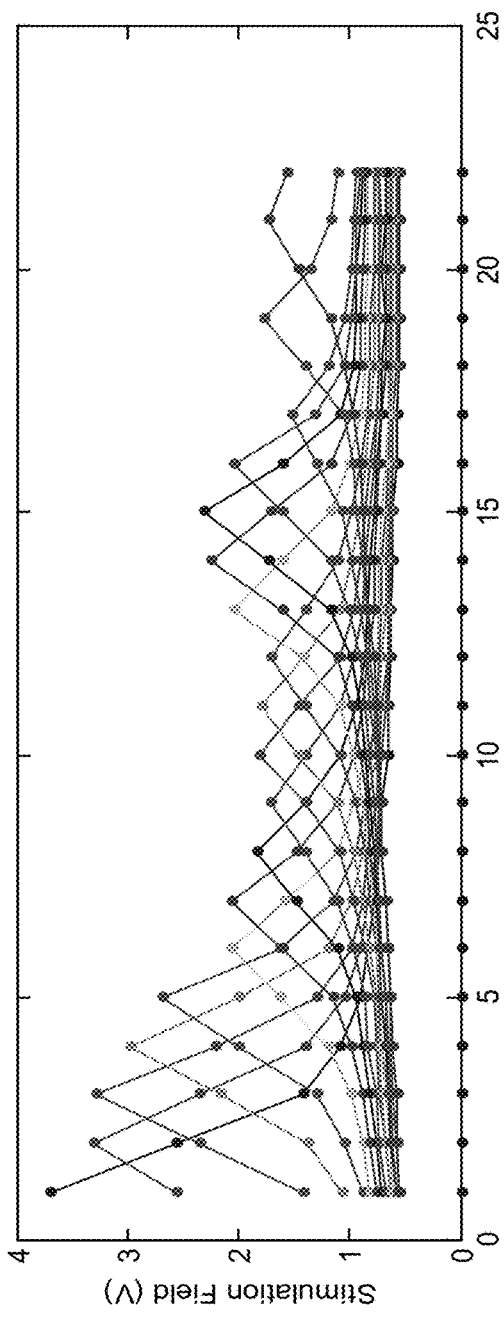
FIG. 15 presents a chart of data obtained according to an exemplary embodiment.
Figure 16:
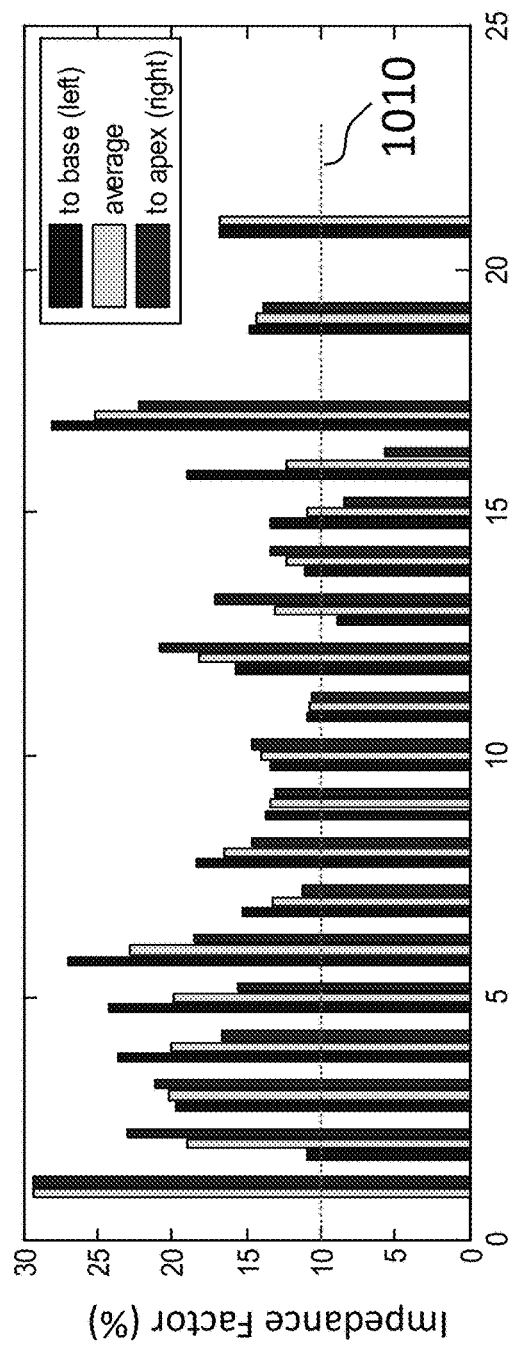
FIG. 16 presents a chart of an analysis of the data of FIG. 15.

Still, with respect to the iterative process, the electrode with the now lowest impedance factor is disabled, this being electrode 22, and method action 510 is reexecuted for all electrodes but with electrode 20 and 22 disabled. FIG. 13 represents the results of such method action in graphical terms. Then, the results are reevaluated, where FIG. 14 represents, again in graphical terms, the results of such reevaluation. As can be seen, electrode 18 still has an average impedance factor below the threshold set at 10%. Again, with respect to the iterative process, the electrode with the now lowest impedance factor is disabled, this being electrode 18, and method action 510 is reexecuted for all electrodes but with electrodes 18, 20, and 22 disabled. FIG. 15 represents the results of such method action in graphical terms. Then, the results are reevaluated, where FIG. 16 represents, again in graphical terms, the results of such reevaluation. As can be seen, now there is no electrode where there exists an average impedance factor below the threshold set at 10%. Accordingly, in an exemplary embodiment, an activation regime of the electrodes of the cochlear implant would entail one where electrodes 1 to 17, 19 and 21 are enabled (i.e., electrodes 18, 20, and 22 are disabled). That said, in an alternate embodiment, the method can be continued until all of the impedance factors are above the threshold value. In this regard, it can be seen from FIG. 16, that electrodes 13, 15, and 16 have impedance factors associated with the basal or apical portions thereof below the threshold value. Accordingly, in an exemplary embodiment, the iterative process may then proceed to, for example, electrode 16 for disablement, etc. Again, it is noted that the average impedance factor was utilized as an exemplary proxy for stimulation spread overlap in this exemplary embodiment. The teachings detailed herein and variations thereof can be implemented utilizing other proxies for which electrodes have the largest overlap/which electrodes have the least utilitarian value with respect to conveying sound information crisply to the auditory nerve, etc. Still further in this regard, it is noted that while this embodiment focuses on the neighboring electrodes, as noted above, in alternate embodiments, the current spread associated with electrodes beyond the neighboring electrodes can also be utilized in the evaluations. Again, any proxy for current spreading that can have utilitarian value can be utilized in some embodiments.

Figure 17:
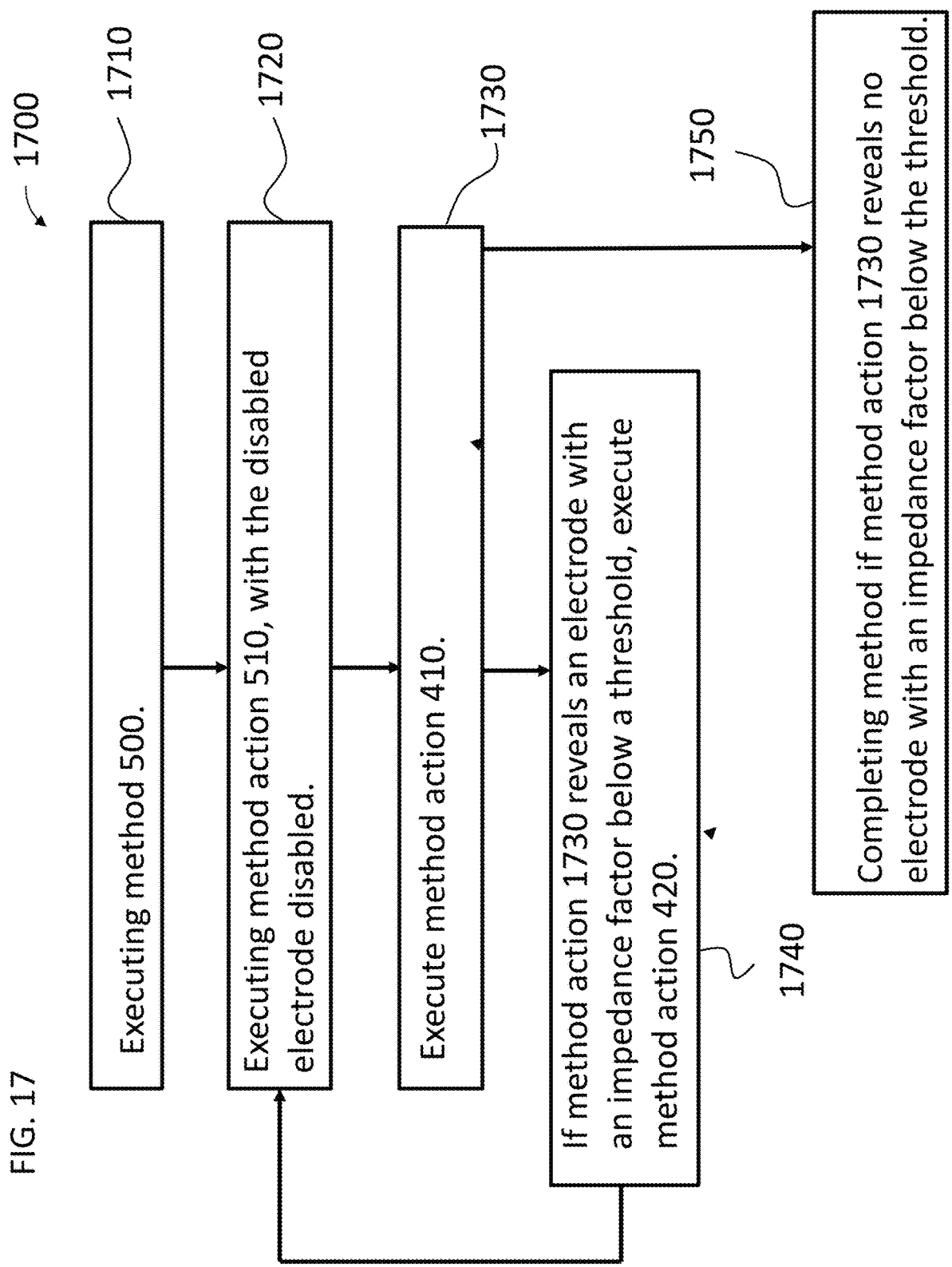
FIG. 17 presents an exemplary flowchart for another exemplary method according to an exemplary embodiment.

Briefly, with respect to the iterative process detailed above, FIG. 17 presents an exemplary flowchart for an exemplary method 1700. Method 1700 is an exemplary method for determining which electrodes of a prosthesis to disable based on current spread within a recipient. As can be seen, method 1700 includes method action 1710, which entails executing method 500. Method 500 is executed with all electrodes active. Method 1700 further includes method action 1720, which entails executing method action 510 with the electrode disabled in method 1710 disabled. By way of example, such a method action would result in the results depicted in FIGS. 11 and 12, where electrode 20 is disabled. In method 1700, after executing method 1720, the method proceeds to method action 1730, which entails executing method action 410 with the data obtained in method action 1720. Here, the method diverges depending on the results of method action 1730. If the result of method action 1730 reveals electrode with an impedance factor below a threshold, method action 420 is executed at method action 1740, and the method returns back to method action 1720, which entails obtaining data with the disabled electrode disabled in method action 1740 disabled. By way of example, such a method action would result in the results depicted in FIGS. 13 and 14, where electrodes 20 and 22 are disabled. The method 1700 continues in this iterative manner until method action 1730 reveals no electrode with an impedance factor below the threshold, at which point the method proceeds to method action 1750 which entails completing the method 1700.

It is briefly noted that while the embodiment presented above utilizes a static threshold (the threshold of a 10% impedance factor value), a dynamic threshold can be utilized in some alternate embodiments. That is, while the same threshold was utilized for each iteration of method 1700, in an exemplary embodiment, a different threshold can be utilized in each iteration. For example, the thresholds may increase with each successive iteration. Alternatively, in an alternate embodiment, the threshold may decrease with each successive iteration. The threshold may increase or decrease exponentially, linearly, etc. Any threshold regime which can have utilitarian value can be utilized in at least some exemplary embodiments.

Thus, in an exemplary embodiment, there is a method for determining which electrodes of a prosthesis to disable based on current spread within a recipient, wherein the method entails iteratively obtaining current spread data for respective electrode energization regimes, wherein the respective electrode energization regimes respectively have more electrodes disabled with respect to the order of iteration.

It is also noted at this time that any of the method actions detailed herein and variations thereof can be implemented in an automatic matter. In an exemplary embodiment, there is a system, such as a fitting system, which is configured to execute the actions of obtaining the respective current spread data for respective electrodes and automatically evaluating the data in an iterative manner, where an additional electrode is disabled in each iteration.

Figure 18:
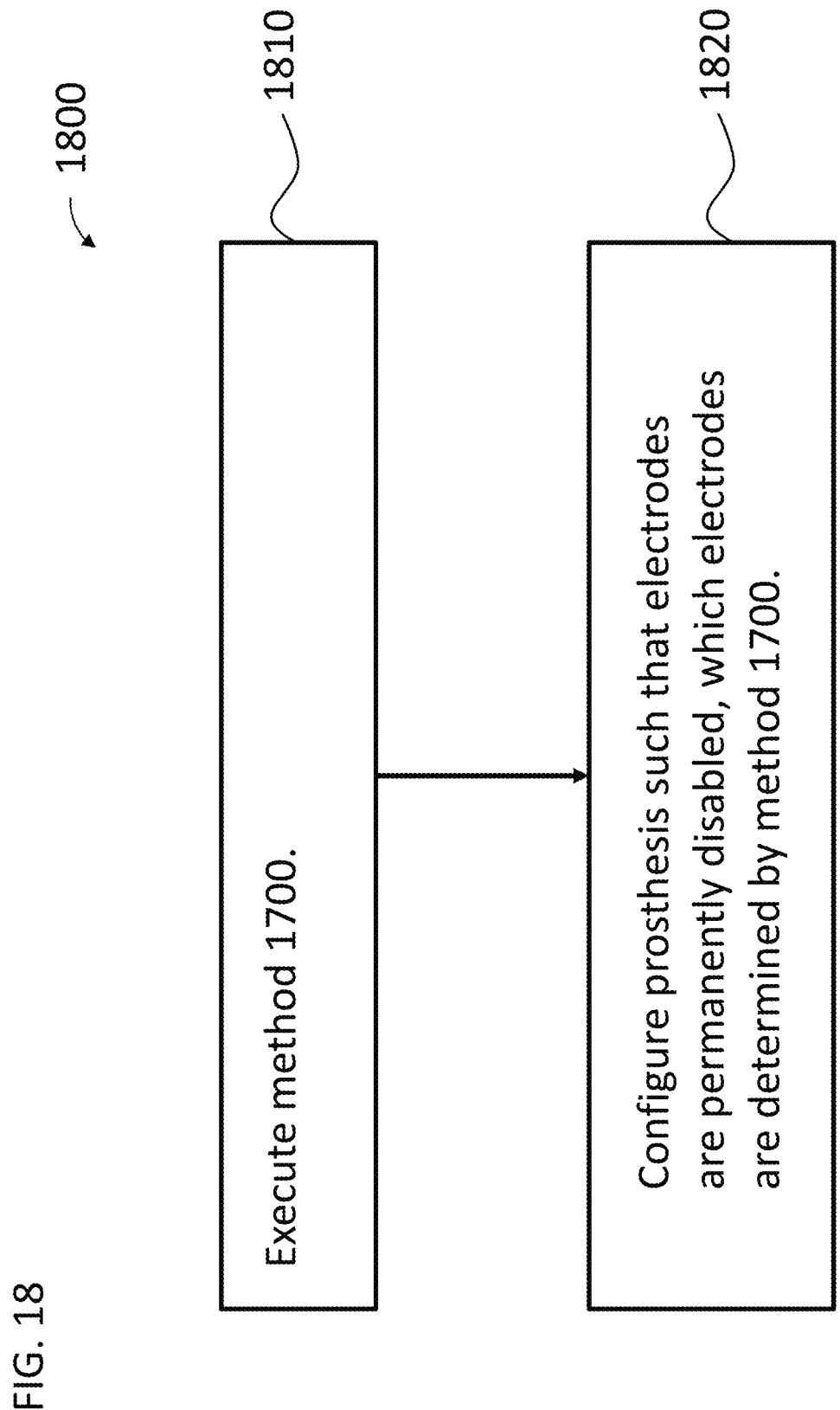
FIG. 18 presents an exemplary flowchart for another exemplary method according to an exemplary embodiment.

FIG. 18 depicts another exemplary method, method 1800. Method 1800 includes method action 1810, which entails executing method 1700. Upon the completion of method action 1810, method action 1800 proceeds to method action 1820, which entails configuring the prosthesis such that the electrodes are permanently disabled, which electrodes are determined by method 1700. In an exemplary embodiment, method action 1820 can be executed by setting a particular map function for the prosthesis, which set particular map function does not utilize the disabled electrodes. In an alternate embodiment, this can entail adjusting a map of the hearing prosthesis so as to not utilize those disabled electrodes. In this regard, method action 1820 can entail creating a map for the hearing prosthesis based on the evaluation of the interactions of respective current spread with one another for the plurality of electrodes implanted in the recipient (e.g., method action 410 as repeated in method 1700) and applying the map to the hearing prosthesis wherein the map, when applied, disables the at least one electrode.

Alternatively, in an exemplary embodiment, the physical properties of the hearing prosthesis can be changed such that stimulation cannot occur from those electrodes. For example, an electrical path between a processor or the like and the electrodes to be disabled can be broken. In an exemplary embodiment, this can entail opening a switch or the like of the prosthesis. Any device, system or method, that will enable electrodes to be deactivated so as to implement the teachings detailed herein can be utilized at least some exemplary embodiments.

While the embodiments detailed above have been directed towards evaluating the interaction of respective current spreads with one another for all the electrodes implanted in the recipient at a localized portion thereof (e.g., those of a single cochlea, as opposed to a scenario where, for example, a recipient has two different cochlear implants, one for each ear—an evaluation of all electrodes implanted in the recipient at a localized portion thereof would not include an evaluation of the electrodes of the other ear, as there would be almost no meaningful overlap between the electrodes of the separate cochlear implants), in some alternate embodiments, the action of evaluating the interaction of respective current spreads with one another is performed for less than all of the electrodes, irrespective of whether or not the electrode array is a so-called short electrode. Thus, in an exemplary embodiment, the action of evaluating interaction of respective current spreads with one another for a plurality of electrodes entails evaluating that for about 25% or more of the localized electrodes, about 30% or more of the localized electrodes, about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more or 100% of the localized electrodes or any value or range of values therebetween in about 1% increments (e.g., 33%, about 49%, 30% to 96%, etc.). In at least the embodiments detailed above, as will be understood, the action of evaluating interaction of respective current spreads with one another entails evaluating interaction of current spreads from at least two electrodes.

Figure 19:
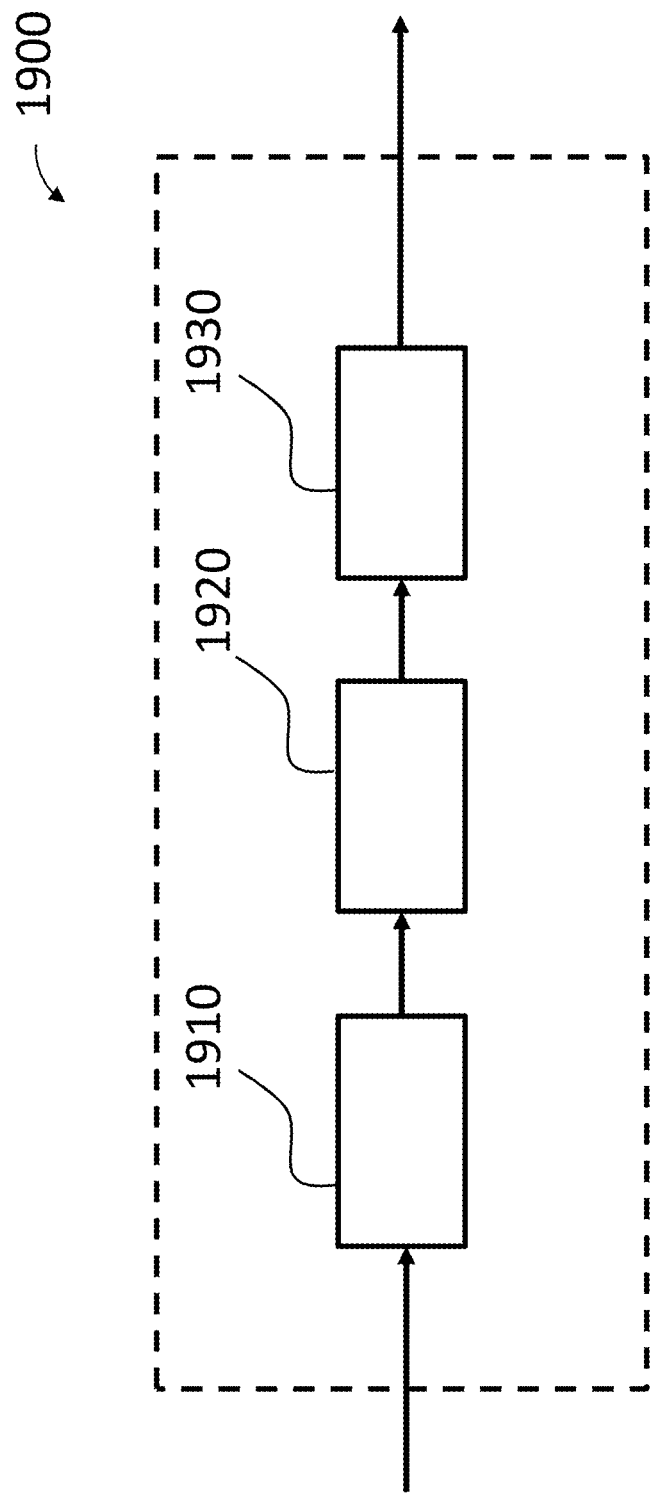
FIG. 19 presents a functional block diagram of an exemplary system according to an exemplary embodiment.

With respect to FIG. 19, in an exemplary embodiment, fitting system 306 can be functionally characterized as a system 1900, comprising a sub-system 1910 configured to obtain respective current spread data for respective electrodes implanted in a recipient (or for respective stimulation channels of a cochlear implant, which respective stimulation channels stimulate tissue at respective locations in the recipient), a sub-system 1920 configured to automatically evaluate that data, and a sub-system 1930 configured to configure a hearing prosthesis based on the evaluation, wherein the configuration of the hearing prosthesis results in the deactivation of at least one of the implanted electrodes (which configuration is represented by output arrow 1930).

In an exemplary embodiment, system 1900 can be a personal computer, a laptop computer, a mainframe computer, a network and/or units connected by a network (as represented by the dashed lines—each component of the system 1900 can be located at separate remote facilities), or a portable computing device (e.g., a smartphone having sufficient computational power), in which case, in some embodiments, system 1900 can correspond to both fitting system 306 and user interface 312 with respect to FIG. 3. System 1900 can alternatively be a portion of one or more of the aforementioned devices. In an exemplary embodiment, sub-system 1910 can obtain the respective current spread data as a result of system 1900 having the functionality to administer the aforementioned electrode energizement and record the resulting voltages (or the resulting eCAP data). In an exemplary embodiment, this can be done autonomously in an interactive manner with the recipient without a clinician operating the machine. Alternatively and/or in addition to this, the system 1900 and/or sub-system 1910 can be operated by a clinician. In an exemplary embodiment, the cochlear implant 100 is configured to execute the aforementioned electrode energizement and voltage recordings (or eCAP recordings) and is configured to store the data therein. In an exemplary embodiment, this data is uploaded or otherwise transferred to sub-system 1920, which could be located at a remote location. Alternatively, in an exemplary embodiment, the cochlear implant is configured to include sub-system 1920. That is, in an exemplary embodiment, the cochlear implant is configured to have the functionality of sub-system 1920. Alternatively, and/or in addition to this, sub-system 1910 can obtain the current spread data as a result of data being uploaded to the system 1900 (e.g., the sub-system 1910 can obtain the data via a USB communication or the like and/or via an ethernet connection or the like and/or via an optical media data storage device etc.). In this regard, unless otherwise specified, as utilized herein, the phrase "obtaining data" encompasses both the action of performing an empirical test to develop the data as well as the action of obtaining data indicative of a prior test without actually executing the empirical test.

In an exemplary embodiment, sub-system 1920 can evaluate the data obtained by sub-system 1910 automatically. In view of the above exemplary methods, in an exemplary embodiment, sub-system 1920 is configured to quantify benefits of respective channels corresponding to the respective electrodes. Moreover, in an exemplary embodiment, the second sub-system is configured to determine which electrodes are more effective at driving neurons, and the second sub-system is configured to identify electrodes to be disabled based on the determination of which electrodes are more effective at driving neurons.

Any device, system, and/or method that will enable the data obtained by sub-system 1910 to be evaluated can be utilized in at least some embodiments, providing that the teachings detailed herein and/or variations thereof can be practiced utilizing such.

To be clear, exemplary embodiments include a system that is configured to execute at least some of the method actions detailed herein. In this regard, in an exemplary embodiment, the first sub-system is configured to measure voltage at the electrodes of the electrode arrays (which excludes the electrode that is energized, at least in some embodiments) and one or both of the first sub-system or the second sub-system is configured to normalize the measured voltage. In this regard, as noted above, in an exemplary embodiment, the energized electrodes can be energized at different current levels corresponding to the fact that different C levels are present for given electrodes. Thus, there is utilitarian value with respect to normalizing the measured voltages so as to obtain an apples to apples comparison. Still further, while some embodiments utilize a C level that is determined for that specific recipient, in some alternate embodiments, a C level estimate is utilized.

Sub-system 1930 is configured to automatically configure the cochlear implant 100 based on the evaluated data via the use of an exemplary algorithm. In an exemplary embodiment, sub-system 1930 is a CPU of a personal computer (such can also be the case with respect to sub-systems 1910 and 1920), or a processor of a portable computing device, or a processor linked to the sub-systems 1910 and 1920 via a network (e.g., internet, etc.). In an exemplary embodiment, sub-system 1930 utilizes an algorithm to develop a map based on the evaluation by sub-system 1920 that will result in the deactivation of one or more of the electrodes/channels. It is further noted that in an exemplary embodiment, sub-system 1930 is part of the cochlear implant. In an exemplary embodiment, the cochlear implant is configured to have the functionality of sub-system 1930. Indeed, in an exemplary embodiment, system 1900 is entirely part of a cochlear implant. Accordingly, in an exemplary embodiment, there is a prosthesis, such as a hearing prosthesis, that utilizes stimulative electrodes, which is configured to have the functionality of system 1900. In an exemplary embodiment, one or more or all of the method actions detailed herein can be executed in an automated fashion by the prosthesis.

It is noted that while the embodiment of FIG. 19 is presented in terms of three distinct sub-systems, it is noted that the phrase sub-system as used herein is not mutually exclusive. In an exemplary embodiment, sub-system 1910, sub-system 1920 and sub-system 1930 can be part of the same sub-system.

With respect to the embodiments that disable certain electrodes, the question then becomes what to do with the content of the channel associated with the disabled/deactivated electrodes. In an exemplary embodiment, the sub-system 1930 is configured to configure the hearing prosthesis such that the channels of the hearing prosthesis corresponding to the deactivated electrodes are at least partially merged with channels that are not deactivated. In an exemplary embodiment, with respect to the above exemplary scenario where electrode 22 is disabled, the contents of that channel can be incorporated into electrode 21. For example, the content of the channels corresponding to electrode 22 will be the lowest frequency content. In an exemplary embodiment, the prosthesis takes the data in that frequency band and applies it in the channel for electrode 21. In an embodiment where there is also content in the channel for electrode 21 owing to the "normal" functionality the hearing prosthesis, the hearing prosthesis can combine the content. In an alternative embodiment, the prosthesis could potentially cancel that original content in the event that the content of the disabled electrode channel has a higher magnitude/amplitude. Any arrangement that can be utilized to present the content of a channel corresponding to a disabled electrode can be utilized in at least some exemplary embodiments.

It is noted that in an exemplary embodiment, the method actions detailed herein associated with the identification of one or more electrodes having utilitarian value with respect to the deactivation thereof can be executed before a traditional fitting method. That is, in an exemplary embodiment, the electrode current interactions can first be evaluated, and then the one or more electrodes having utilitarian value with respect to deactivation can be deactivated, and then the traditional fitting method can be implemented. In an exemplary embodiment, the stimulation currents that are applied could be sub threshold, at least in the embodiments utilizing eCAP. That said, in at least some exemplary embodiments, the stimulation currents that are applied could be supra threshold. Still, some embodiments will have utilitarian value with respect to utilizing C level currents. Note further, in some exemplary embodiments, levels corresponding to those just above the C levels are utilized. Any current level that can enable the teachings detailed herein and/or variations thereof can be utilized in at least some exemplary embodiments.

That said, because of the utilitarian value with respect to utilizing C level currents, in an exemplary embodiment, the methods associated with respect to the identification of one or more electrodes have utilitarian value with respect to the deactivation thereof can be executed as part of/an addition to a traditional fitting method. In this regard, an exemplary traditional fitting method may first set out to identify the T and C levels for each electrode channel. In an exemplary embodiment, after this is executed (e.g., the C levels are found), the C levels are utilized in method 1700 as the current levels utilized to energize each electrode. Then, upon the determination of which electrodes are to be deactivated, those electrodes are deactivated, and then the fitting method proceeds therefrom in the traditional manner with those channels deactivated. The action of merging the content of a deactivated channel with a non-deactivated channel can be executed prior to further proceeding in the fitting method, or as an action that is executed after the end of the traditional fitting method.

Figure 20:
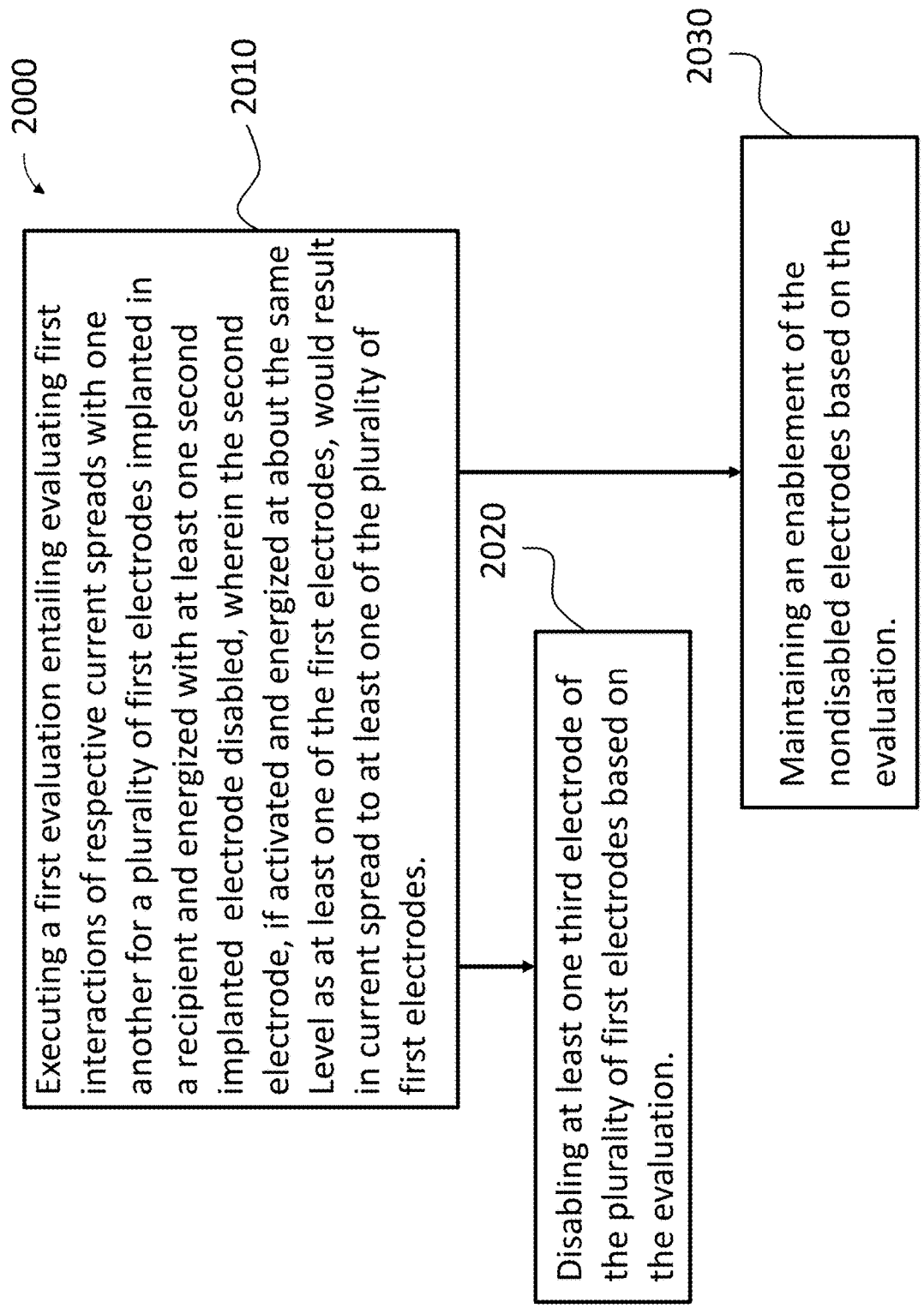
FIG. 20 presents an exemplary flowchart for another exemplary method according to an exemplary embodiment.

FIG. 20 presents a flowchart for another exemplary method, method 2000, which utilizes at least some of the teachings detailed above. Method 2000 includes method action 2010, which entails executing a first evaluation including evaluating first interactions of respective current spreads with one another for a plurality of first electrodes implanted in a recipient resulting from energizement thereof with at least one second implanted electrode disabled, wherein the second electrode, if enabled and energized at about the same level (which includes the same level) as at least one of the first electrodes, would result in current spread to at least one of the plurality of first electrodes. In an exemplary embodiment, with reference to FIGS. 11 and 12, the first electrodes correspond to electrodes 1-19 and 21-22, and the at least one second electrode corresponds to electrode 20 (the disabled electrode). As can be seen from FIG. 9, electrode 20 would result in current spread to at least one of electrodes 1-19 and 21-22.

Method 2000 further includes method action 2020 and method action 2030. Method action 2120 entails disabling at least one third electrode of the plurality of first electrodes based on the evaluation. With respect to FIGS. 11-14, this would entail the deactivation of electrode 22. Method action 2030 entails maintaining an enablement of the nondisabled electrodes based on the evaluation. With respect to FIGS. 11-16, this would entail ending method 1700 because all of the impedance factors are above the 10% threshold. As can be seen, method action 2030 and method action 2020 are optional method actions with respect to a given temporal instant (it is to be appreciated that in an exemplary embodiment, method action 2020 is executed, and then a revaluation occurs with the disabled electrode, and then method action 2030 could be executed).

Of course, in an exemplary embodiment, prior to executing method 2000 in general, or prior to the execution of method action 2021, an exemplary embodiment entails executing a second evaluation including evaluating second interaction of respective current spreads with one another for a plurality of electrodes including the first electrodes and the at least one second electrode in a non-disabled state (e.g., this can correspond to FIGS. 9 and 10, and disabling the at least one second electrode (electrode 20) based on the second evaluation.

With respect to the iterative nature of some of the methods detailed herein, in an exemplary embodiment, there is a method that includes executing a third evaluation after the first evaluation including evaluating third interaction of respective current spreads with one another for the plurality of first electrodes resulting from energizement thereof with at least the second electrode and the third electrode disabled. For example, with respect to FIGS. 13 and 14, electrodes 1-19 and 21 are enabled, and electrodes 20 and 22 are disabled (corresponding to the second electrode and the third electrode), wherein the third electrode, if enabled and energized at about the same level as at least one of the first electrodes would result in current spread to at least one of the plurality of first electrodes (as represented by FIG. 11). This exemplary method further includes disabling at least fourth electrode based on the third evaluation (e.g., electrode 18 with respect to FIGS. 15 and 16) or maintaining an enablement of the nondisabled electrodes based on the third evaluation (e.g., the evaluation determines that all impedance factors for the enabled electrodes are above the threshold level, and thus no further deactivation is warranted or otherwise deemed utilitarian).

Figure 21:
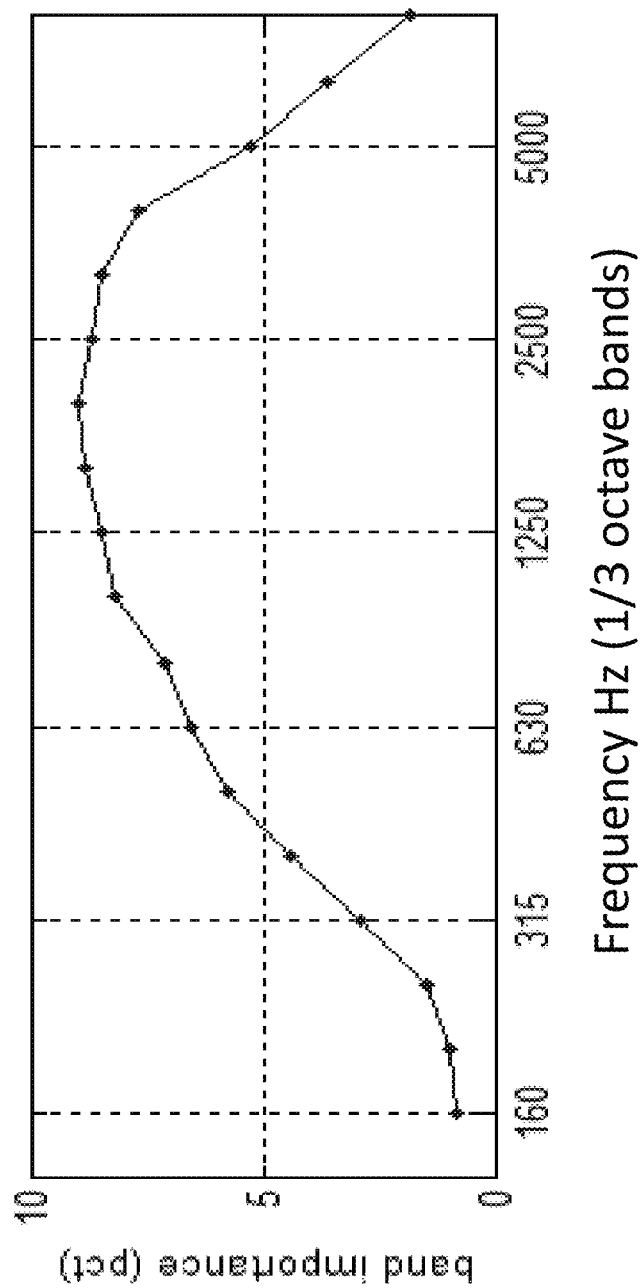
FIG. 21 presents an exemplary graph detailing band importance with respect to speech understanding for a statistically significant group of normal hearing listeners.
Figure 22:
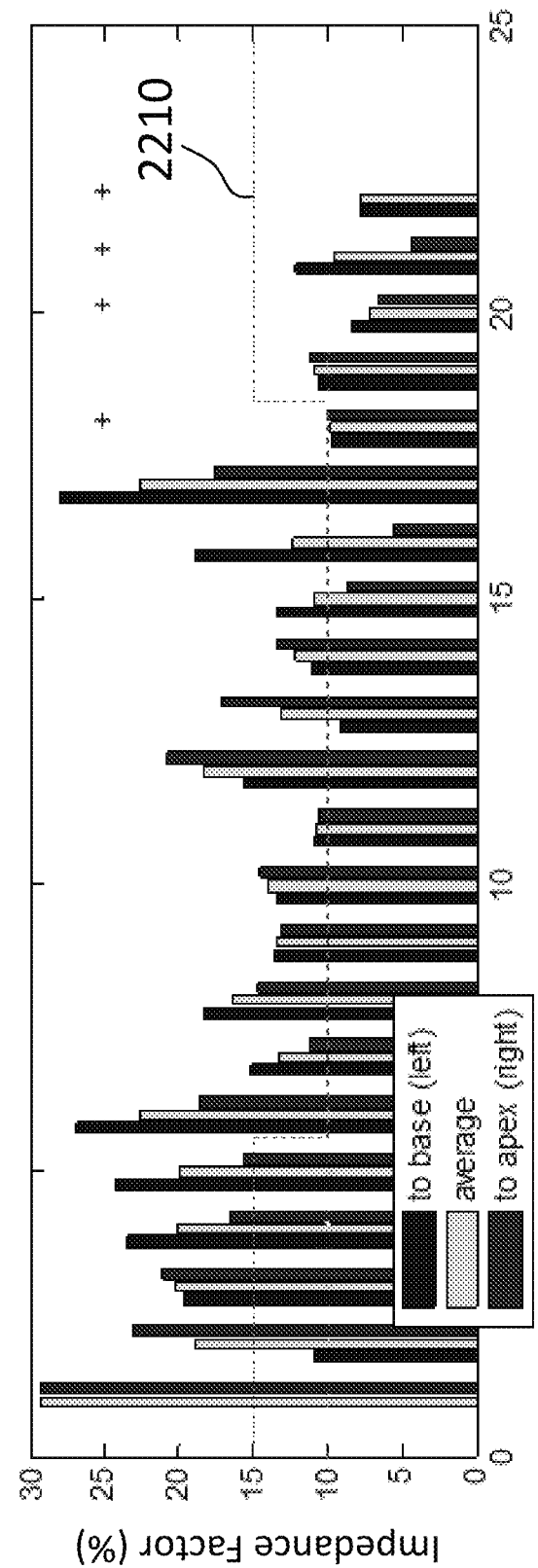
FIG. 22 presents a chart of data obtained according to an exemplary embodiment.

In an exemplary embodiment, the teachings detailed herein associated with determining which electrodes of the prosthesis to disable can also be based on the importance of frequency bands for such things as speech intelligibility (or for vision understanding in the case of retinal implants). FIG. 21 presents an exemplary chart presenting the importance of various frequency bands with respect to speech intelligibility for normal hearing listeners. As can be seen, in an exemplary embodiment, the frequencies below 315 Hz, and above 5000 Hz are relatively less important than the frequencies therebetween. Accordingly, in an exemplary embodiment, such may entail disabling the channels associated with the frequencies below 315 Hz and above 5000 Hz if such channels resulted in the impedance factors below 20%, and disabling the channels associated with the frequencies and between. That is, in an exemplary embodiment, the threshold detailed above is not the same for each channel. An exemplary threshold is seen in FIG. 22, where threshold line 2210 is superimposed over the data corresponding to FIG. 10. As can be seen, threshold line 2210 extends at the 15% threshold level to a location basal electrode 19, and then extends a 10% to a position apical electrode 5, and then extends at 15% thereafter, although such could extend at 10% thereafter, or at 17.5% thereafter, etc. Any threshold that can have utilitarian value can be practiced in at least some exemplary embodiments.

In an alternate embodiment, instead of adjusting threshold level, weights can be applied to the given channels. For example, the channels for providing frequencies at and above 315 Hz, and at and below 5 kHz can be provided a first weighting, and the channels for providing frequencies below 315 Hz and above 5 kHz can be provided with a second weighting less than the first weighting, etc. That said, in an exemplary embodiment, the weightings according to the chart on FIG. 21 can be utilized. For example, the results of equation (3) can be multiplied by the percentage for that given frequency band associated with the chart of FIG. 21. Any arrangement that can enable the establishment of privacy with respect to the importance of a given electrode can be utilized at least some exemplary embodiments.

That said, in some embodiments, the teachings detailed herein are restricted to weighting the electrodes based solely on spreading functions/relying solely on the electrode impedance factor for determining which electrodes to disable.

While the above has focused on the embodiment where the electrodes are disabled permanently, in an alternate embodiment, the electrodes are instead disadvantaged relative to others and/or some electrodes are advantaged relative to others. In an exemplary embodiment, this could entail multiplying the stimulation current applied at a given electrode with the aforementioned weighting values of equation (3) developed for each of the electrodes. This would disadvantage some and also advantage others. Alternatively, a pure disadvantaged regime can be utilized, where, for example, the electrodes are identified as being candidates for disablement because they are below the various thresholds are instead disadvantaged by a predetermined percentage (e.g., 50%, 33%, 75%, etc.). In an exemplary embodiment, the disadvantages could be equally applied to all of the subject electrodes, while in alternate embodiments, a linear or an exponentially increasing disadvantaged regime can be utilized. For example, with respect to the exemplary embodiment of FIGS. 9-16, electrode 20 could be subject to a 75% disadvantage (i.e., the current is reduced by 75% from that which would otherwise be the case), the electrode 22 could be subject to a 50% disadvantage, and electrode numeral 18 could be subject to a 25% advantage. As can be seen, the higher disadvantages apply to the electrode with the biggest overlap/least independence. Still further by example, with respect to the exemplary embodiment of FIGS. 9-16, electrode 20 could be subject to a 90% disadvantage (i.e., the current is reduced by 90% from that which would otherwise be the case), the electrode 22 could be subject to a 70% disadvantage, and electrode numeral 18 could be subject to a 20% advantage. (Of course, the results of the iterations would be different, because in some of removing a channel completely from the iterative process, the channel is simply disadvantaged, so it is possible that the just described exemplary scenarios might result in different electrodes being disadvantaged.) Still further, in some embodiments, the least independent electrodes could be disabled, and other electrodes could be disadvantaged. Any system or method that can enable the teachings detailed herein to have utility can be utilized in at least some exemplary embodiments.

As noted above, while the teachings detailed herein have primarily focused on the utilization of current spread, utilitarian value can be achieved utilizing neural spread functions. In an exemplary embodiment, data that is an equivalent to the data corresponding to FIGS. 6, 7, 8, 9, 10, 11, 12, 13, 14, 15, and 16 can be obtained utilizing an eCAP system. In this regard, in an exemplary embodiment, the cochlear implant 100 includes a fully integrated eCAP system. Alternatively, a separate eCAP system can be implanted in the recipient. Any arrangement that can obtain neural telemetry can be utilized in at least some exemplary embodiments, just as is the case with respect to the EVT measurements detailed herein. In an exemplary embodiment, NRT is utilized to develop neural spread functions in a manner analogous to that applied above to develop the EVT functions. The data based on this developed neural spread functions is then evaluated, again in a manner analogous to that detailed above, and based on this evaluation, the electrodes to deactivate and/or to disadvantage are identified. In an exemplary embodiment, the utilization of NRT enables data to be obtained that is based on the passive current that affects the auditory nerves and the like. That is, unlike the utilization of the EVT measurements detailed above, there is no current offset that is inherent in all of the spread functions.

Thus, according to the teachings detailed herein, there are methods and devices and systems that enable the interaction between electrodes to be documented based on EVT and/or on NRT. Indeed, it is noted that in at least some exemplary embodiments, both neural spread functions and electrical spread functions can be utilized at the same time to develop the impedance factors/weighting for the given electrodes. For example, the results of the evaluation utilizing the electrical spread functions can be averaged with the results of the evaluation utilizing the neural spread functions. For example, if an electrode received a weighting score of 0.35 using the electrical spread function algorithms, and received a weighting score of 0.3 utilizing the neural spread function algorithms, the combined weight could be 0.325. Alternatively, such combined implementations can favor one type of implementation over the other (e.g., weighting one score twice as much as the other etc.).

That said, in an exemplary embodiment, the methods detailed herein and/or variations thereof can include the method action of determining which of EVT or NRT is more likely to produce utilitarian results, and proceeding utilizing the data collected or otherwise obtained utilizing the system that is more likely to produce utilitarian results. In an exemplary embodiment, this can be performed based on a statistical analysis of characteristics of the recipient, where only one system is utilized to obtain data. Alternatively, data is obtained utilizing both systems, and the data is triaged to determine which data is the most promising data to be utilized in the methods herein. Still further, in an exemplary embodiment, an electrode enablement and/or disablement regime can be developed utilizing the data based on the EVT, and another electrode enablement and/or disablement regime can be developed utilizing data based on the NRT, and both can be implemented in a serial fashion, and the recipient can choose which one is more desirable.

It is noted that in at least some exemplary embodiments, some or all of the method actions detailed herein and/or variations thereof can be executed within a half hour from start to finish. In an exemplary embodiment, some or all of the method actions detailed herein and/or variations thereof can be executed within 10 minutes, 15 minutes, 20 minutes, 25 minutes, 30 minutes, 35 minutes, 40 minutes, 45 minutes, 50 minutes, 55 minutes, one hour, 1.25 hours, 1.5 hours, 1.75 hours, two hours, three hours, or less.

It is briefly noted that the embodiments detailed herein do not utilize long-term speech spectrums/calculations or the like. Thus, in an exemplary embodiment, there is a method that includes any of the method actions detailed herein and/or variations thereof, that is executed without utilizing long-term speech spectrums/calculations. Still further, in an exemplary embodiment, the teachings detailed herein do not require or otherwise utilize a CAT scan or other imaging techniques to determine the location of the implant relative to tissue of the recipient. Accordingly, in an exemplary embodiment, there is a method that includes any of the method actions detailed herein and/or variations thereof, that is executed without utilizing a CAT scan that images the placement of the prosthesis relative to tissue of the recipient.

In view of the above, it can be seen that in at least some exemplary embodiments, according to the teachings detailed herein, there is a prosthesis, such as the hearing prosthesis, such that signals provided to the tissue of the recipient come from fewer sources at larger distances than that which would otherwise be the case for that exact same prosthesis implanted in exactly the same location all other things being equal.

Some embodiments detailed herein have utilitarian value in that the optimization of the electrode subset can be executed without utilizing such things as pitch discrimination or temporal ripple discrimination or multipolar thresholds. Accordingly, in an exemplary embodiment, some or all of the method actions detailed herein and/or variations thereof are executed without reliance on or otherwise collecting psychoacoustic measures such as pitch discrimination, temporal ripple discrimination, or multipolar thresholds.

Still further, some exemplary embodiments detailed herein can have utilitarian value with respect to optimizing the electrode subset at a time where the implant user has not yet learned to discriminate fine details of the electrical stimulation and/or where the implant user is a child or person with limited cognitive capabilities and/or limited ability to convey or communicate what he or she senses. In an exemplary embodiment, the teachings detailed herein can be implemented on a recipient that does not have the ability to reliably detect the stimulus. Corollary to this is that the teachings detailed herein can be practiced on the recipient that does not have the ability to reliably detect that stimulus.

Also, some exemplary embodiments detailed herein can have utilitarian value with respect to maintaining or otherwise avoiding a change in an electrical tonotopy to which the recipient has been accustomed. In this regard, the teachings detailed herein can be implemented at a time early in the recipient's hearing journey. By way of example only and not by way of limitation, some or all of the method actions detailed herein can be executed within 1 week, 2 weeks, 3 weeks, 4 weeks, 5 weeks, 6 weeks, 7 weeks, 8 weeks, 9 weeks, 10 weeks, 11 weeks, or 12 weeks of the implantation of the cochlear implant.

As noted above, at least some of the method actions can be executed at a location remote from where another method action is located. For example, it is noted that an exemplary embodiment entails executing some or all of the method actions detailed herein, where the recipient of the hearing prosthesis is located remotely (e.g., geographically distant) from where at least some of the method actions detailed herein are executed (e.g., any method action detailed herein that can be executed by, for example, a computer or other processor located at a remote location). For example, any of the methods detailed herein could be executed via internet communication with the hearing prosthesis and the user interface 314 and/or the hearing implant fitting system 306 (e.g., communication link 308 of FIG. 3 can be an internet connection or a wired or wireless connection). Still further by example, with respect to a given method, one or more method actions can be executed at one location (controlled by the audiologist 304 at another location geographically remote from the one location), and one or more other method actions can be executed at the location where the audiologist 304 is located. That is, any method action herein can be executed at one location, and any method action herein can be executed at another location, and so on, providing that the teachings detailed herein and/or variations thereof can be practiced.

It is further noted that in an alternate embodiment, one or more of the method actions detailed herein are executed by the recipient of the cochlear implant. Indeed, in an exemplary embodiment, there is a system that enables a recipient to execute, in conjunction with the system, the method actions detailed herein such that the cochlear implant can be "remapped" (electrodes disabled, enabled, disadvantaged, advantaged, etc.) without any additional input from a clinician or the like.

The above embodiments have been directed towards a static regime where the electrodes/channels that are disabled or disadvantaged are disabled or disadvantaged in a substantially permanent manner (e.g., at the time of fitting). This can be considered static disablement/static disadvantaging. Note that this does not foreclose the ability to later make adjustments so as to reenable a given electrode and/or adjust or eliminate any disadvantaging of a given electrode. The concept here is that for a substantial period of time (e.g., a period of months), the electrodes are disabled and/or otherwise disadvantaged. That said, in an alternate embodiment, the teachings detailed herein can be utilized in a dynamic manner (dynamic disablement/dynamic disadvantaging). By way of example, the disablement and/or disadvantaging can be sound scenario specific. For example, a given sound that is captured could be such that the frequencies that are implicated do not result in overlap and/or any overlap is deminimis. For example, a scenario where a sound that is captured has significant frequency content at 500 Hz and below, and significant frequency content at 1500 Hz and above, but little content in between, could be a scenario where little to no overlap will occur as a result of activation of channels that would otherwise be deactivated in the static application because the channels will be widely separated from each other. Still further by exemplary scenario, a captured sound could have a very narrow bandwidth, thus meaning that the neighbors of a given electrode that is activated to evoke a hearing percept based on the sound that is captured will not be activated or otherwise activated to produce a very minimal output. Thus, even if the given electrode/channel is one that is a candidate for deactivation and/or for disadvantaging based on the teachings detailed herein, if the dynamic nature of the captured sound is such that there is a very low likelihood that deleterious effects of overlap will occur, the electrode would not be deactivated or otherwise disadvantaged. Alternatively, in a scenario where the sound is relatively broad-based with respect to frequency, and thus the neighbors of a given electrode channel that is activated to evoke a hearing percept will also be activated or otherwise activated produce a relatively significant output, that given electrode channel known to create the overlap could be deactivated or otherwise disadvantaged during that sound scenario.

Indeed, in keeping with the above embodiment, the default could be to deactivate or otherwise disadvantage the particular channels, and only counteract their deactivation/disadvantaging upon a determination that the captured sounds, when processed and broken up into the various channels by the sound processor, would not likely result in the overlap (alternatively, the opposite could be the default in other embodiments). In an exemplary embodiment, the disadvantaging can be dynamic. That is, depending on the given sound that is captured, the percentage or weighting that is applied to a given electrode channel so as to disadvantage that given electrode channel could be variable. For example, in a scenario where the sound is relatively narrowly confined to frequencies corresponding to a single electrode channel, the disadvantaging of that channel could be zero or near zero. Conversely, in an exemplary scenario where the sound is narrowly frequency based, but such that it will result in the activation of a limited number of channels adjacent to one another (in the absence of the disabling and/or disadvantaging of the channel(s)), the given channel could be deactivated and/or disadvantaged by an amount that is much higher (e.g., 75% reduction in current from that which would otherwise be the case). Conversely, in an exemplary scenario where the sound is relatively more broad-based, and thus the resulting processing will activate the particular channel and neighboring channels and other channels, the disadvantaging could be in between (e.g., 30%-50% reduction in current from that which would otherwise be the case). That said, if it is found that there is utilitarian value in using a lower reduction in current for the former scenario and using a higher reduction in current for the later scenario, that also could be applied. Note that the aforementioned scenarios are simply presented for purposes of conveying the concept that the teachings detailed herein can be utilized in a dynamic manner.

Thus, an exemplary embodiment entails continuously monitoring in real time the inputs into the sound processor or the like, and increasing and/or decreasing the amount that a particular channel is disadvantaged based on the impact of a given electrode channel known to create overlap if the channel was not disadvantaged or otherwise disadvantaged according to a predetermined setting.

In an exemplary embodiment, the prosthesis is configured so as to implement a dynamic peak picking scheme where the channels having relatively greater overlap are disadvantaged. In an exemplary embodiment, respective stimulation currents for given channels are disadvantaged by a given amount, and this is done computationally prior to sorting the various values to determine maxima, such as is done in the ACE sound processing strategy. Then, the maxima is determined and the ACE sound processing strategy is implemented to evoke a hearing percept.

It is noted that any disclosure of a method action detailed herein corresponds to a disclosure of a corresponding system and/or device for executing that method action, in at least some embodiments, automatically. It is further noted that any disclosure of an apparatus or system herein corresponds to a disclosure of a method of operating that apparatus. It is also noted that any disclosure of any method action detailed herein further includes a disclosure of executing that method action in an automated fashion, as well as a device for executing those method actions in the automated manner and/or in a non-automated manner. Also, any disclosure of a method of making a device/system corresponds to a disclosure of the resulting device/system, and visa-versa.

It is further noted that any disclosure of a fitting method herein corresponds to a hearing prosthesis or hearing device fitted according to that method.

Also, it is noted that exemplary embodiments can include non-transitory computer readable medium(s) having recorded thereon, a computer program for executing a method, program including code for automatically executing one or more of the method actions detailed herein.

In another exemplary embodiment, there is a method, comprising evaluating least one of interactions of respective current spreads with one another or interactions of respective neural spreads with one another for a plurality of electrodes implanted in a recipient; and disabling or disadvantaging at least one electrode based on the evaluation, wherein the action of evaluating least one of interactions of respective current spreads with one another or interactions of respective neural spreads with one another for a plurality of electrodes implanted in a recipient includes evaluating interaction of current from at least two electrodes of the plurality of electrodes and not evaluating interaction of current from at least one other electrode of the plurality of electrodes.

In another exemplary embodiment, there is a method, comprising evaluating least one of interactions of respective current spreads with one another or interactions of respective neural spreads with one another for a plurality of electrodes implanted in a recipient; and disabling or disadvantaging at least one electrode based on the evaluation, and the method further comprises disabling at least two electrodes based on the evaluation. In another exemplary embodiment, there is a method, comprising evaluating least one of interactions of respective current spreads with one another or interactions of respective neural spreads with one another for a plurality of electrodes implanted in a recipient; and disabling or disadvantaging at least one electrode based on the evaluation, wherein the action of evaluating least one of interactions of respective current spreads with one another or interactions of respective neural spreads with one another for a plurality of electrodes implanted in a recipient includes evaluating interaction of neural excitation resulting from the energizement of at least two electrodes with respective electrodes of the plurality of electrodes.

In another exemplary embodiment, there is a method, comprising evaluating least one of interactions of respective current spreads with one another or interactions of respective neural spreads with one another for a plurality of electrodes implanted in a recipient; and disabling or disadvantaging at least one electrode based on the evaluation, wherein the action of evaluating least one of interactions of respective current spreads with one another or interactions of respective neural spreads with one another for a plurality of electrodes implanted in a recipient includes evaluating interaction of current from neighboring electrodes with respective electrodes of a plurality of electrodes.

In another exemplary embodiment, there is a fitting system, comprising: a first sub-system configured to obtain respective spread function data for respective electrodes implanted in a recipient; a second sub-system configured to automatically evaluate the data; and a third sub-system configured to configure a hearing prosthesis based on the evaluation, wherein the configuration of the hearing prosthesis results in the disablement of at least one of the implanted electrodes, wherein a third sub-system configured to configure the hearing prosthesis such that channels of the hearing prosthesis corresponding to the deactivated electrodes are at least partially merged with channels that are not deactivated.

In another exemplary embodiment, there is a fitting system, comprising: a first sub-system configured to obtain respective spread function data for respective electrodes implanted in a recipient; a second sub-system configured to automatically evaluate the data; and a third sub-system configured to configure a hearing prosthesis based on the evaluation, wherein the configuration of the hearing prosthesis results in the disablement of at least one of the implanted electrodes, wherein the fitting system is configured to execute the actions of obtaining the respective spread function data for respective electrodes and automatically evaluating the data in an iterative manner, where an additional electrode is disabled in each iteration.

In another exemplary embodiment, there is a non-transitory computer readable medium having recorded thereon, a computer program for executing a method, the program including: code for automatically determining which electrodes of a prosthesis to enable based on spread functions within a recipient, wherein the code for automatically determining which electrodes of a prosthesis to enable disables electrodes based on those that have the lowest result from the division.

While various embodiments of the present invention have been described above, it should be understood that they have been presented by way of example only, and not limitation. It will be apparent to persons skilled in the relevant art that various changes in form and detail can be made therein without departing from the scope of the invention.

FIGS. 23-30 contain schematics detailing various method actions according to exemplary embodiments, where FIG. 23 includes block 2310 including method actions, FIG. 22 includes block 2210 including method actions, FIG. 25 includes block 2510 including method actions, FIG. 26 includes block 2610 including method actions, FIG. 27 includes block 2710 including method actions, FIG. 28 includes block 2810 including method actions, FIG. 29 includes block 2910 including method actions, and FIG. 30 includes block 3010 including method actions.

What is claimed is:

1. A method, comprising:
evaluating at least one of interactions of respective current spreads with one another or interactions of respective neural spreads with one another for a plurality of electrodes implanted in a recipient;
disabling or disadvantaging at least one electrode based on the evaluation;
applying electrical current to the electrodes of the plurality of electrodes to generate the respective current spreads and/or to evoke the neural spreads;
using in-vivo electrode voltage telemetry (EVT) to obtain data to enable the evaluation of the at least one of interactions of respective current spreads with one another or interactions of respective neural spreads with one another for the plurality of electrodes implanted in a recipient, wherein
the action of evaluating the at least one of interactions of respective current spreads with one another or interactions of respective neural spreads with one another for the plurality of electrodes implanted in a recipient includes comparing voltage based data of the obtained data.

2. The method of claim 1, further comprising:
obtaining data indicative of at least one of respective current spreads or respective neural spreads for the plurality of electrodes; and
basing the evaluation on the obtained data.

3. The method of claim 2, wherein:
the action of obtaining data indicative of at least one of respective current spreads or respective neural spreads for the plurality of electrodes includes obtaining respective neural spreads for the plurality of electrodes.

4. The method of claim 1, wherein:
the electrodes are electrodes of a hearing prosthesis.

5. The method of claim 3, further comprising:
creating a map for the hearing prosthesis based on the evaluation, and
applying the map to the hearing prosthesis, wherein the map, when applied, disables or disadvantages the at least one electrode.

6. The method of claim 5, wherein:
the action of disabling or disadvantaging the at least one electrode based on the evaluation includes disadvantaging the at least one electrode based on the evaluation.

7. The method of claim 4, further comprising:
creating a map for the hearing prosthesis based on the evaluation, and
applying the map to the hearing prosthesis, wherein the map, when applied, disadvantages the at least one electrode.

8. The method of claim 1, wherein:
evaluating at least one of interactions of respective current spreads with one another or interactions of respective neural spreads with one another for a plurality of electrodes implanted in a recipient includes doing so for at least 6 electrodes.

9. The method of claim 1, wherein:
the action of evaluating at least one of interactions of respective current spreads with one another or interactions of respective neural spreads with one another for a plurality of electrodes implanted in a recipient includes evaluating interaction of current from at least two electrodes with respective electrodes of the plurality of electrodes.

10. The method of claim 1, wherein:
the action of disabling or disadvantaging at least one electrode based on the evaluation is executed as part of a dynamic sound processing regime.

11. The method of claim 1, further comprising:
automatically determining which of the electrodes of the prosthesis to disable based on the evaluation utilizing a processor.

12. The method of claim 1, further comprising:
automatically disabling or disadvantaging at least one of the electrodes based on the evaluation.

13. The method of claim 1, wherein:
the action of evaluating at least one of the interactions of respective current spreads with one another or interactions of respective neural spreads with one another for a plurality of electrodes implanted in a recipient is executed automatically.

14. The method of claim 1, wherein:
the action of evaluating at least one of interactions of respective current spreads with one another or interactions of respective neural spreads with one another for the plurality of electrodes implanted in the recipient includes evaluating interaction of current from at least two electrodes of the plurality of electrodes and not evaluating interaction of current from at least one other electrode of the plurality of electrodes.

15. The method of claim 1, further comprising:
disabling at least two electrodes implanted in the recipient based on the evaluation.

16. The method of claim 1, wherein:
the action of evaluating at least one of interactions of respective current spreads with one another or interactions of respective neural spreads with one another for the plurality of electrodes implanted in a recipient includes evaluating interaction of neural excitation resulting from the energizement of at least two electrodes of the plurality of electrodes with respective electrodes of the plurality of electrodes.

17. The method of claim 1, wherein:
the action of disabling or disadvantaging the at least one electrode based on the evaluation includes disadvantaging the at least one electrode based on the evaluation.

18. The method of claim 1, wherein:
the action of disabling or disadvantaging the at least one electrode based on the evaluation includes disadvantaging the at least one electrode based on the evaluation and not disabling or disadvantaging at least one electrode.

19. The method of claim 1, wherein:
the action of disabling or disadvantaging the at least one electrode based on the evaluation includes disadvantaging the at least one electrode and then disabling the at least one electrode based on the evaluation.

20. The method of claim 1, wherein:
evaluating at least one of interactions of respective current spreads with one another or interactions of respective neural spreads with one another for the plurality of electrodes implanted in a recipient includes doing so for at least 6 electrodes, and wherein the action of evaluating at least one of interactions of respective current spreads with one another or interactions of respective neural spreads with one another includes evaluating interactions of respective neural spreads with one another.

21. The method of claim 1, wherein:
evaluating at least one of interactions of respective current spreads with one another or interactions of respective neural spreads with one another for the plurality of electrodes implanted in a recipient includes:
evaluating at least one of interactions of respective current spreads with one another or interactions of respective neural spreads with one another for a first and a second electrode implanted in the recipient;
evaluating at least one of interactions of respective current spreads with one another or interactions of respective neural spreads with one another for a third and a fourth electrode implanted in the recipient;
evaluating at least one of interactions of respective current spreads with one another or interactions of respective neural spreads with one another for a fifth and a sixth electrode implanted in the recipient;
evaluating at least one of interactions of respective current spreads with one another or interactions of respective neural spreads with one another for a seventh and a eighth electrode implanted in the recipient;
evaluating at least one of interactions of respective current spreads with one another or interactions of respective neural spreads with one another for a ninth and a tenth electrode implanted in the recipient; and
evaluating at least one of interactions of respective current spreads with one another or interactions of respective neural spreads with one another for an eleventh and a twelfth electrode implanted in the recipient.

22. The method of claim 21, wherein:
evaluating at least one of interactions of respective current spreads with one another or interactions of respective neural spreads with one another for a plurality of electrodes implanted in a recipient includes:
evaluating at least one of interactions of respective current spreads with one another or interactions of respective neural spreads with one another for a thirteenth and a fourteenth electrode implanted in the recipient;
evaluating at least one of interactions of respective current spreads with one another or interactions of respective neural spreads with one another for a fifteenth and a sixteenth electrode implanted in the recipient;
evaluating at least one of interactions of respective current spreads with one another or interactions of respective neural spreads with one another for a seventeenth and an eighteenth electrode implanted in the recipient.

23. The method of claim 1, further comprising:
not evaluating interaction of current from at least one other implanted electrode with the respective electrodes of the plurality of electrodes.

24. The method of claim 1, further comprising:
obtaining data indicative of respective current spreads for the plurality of electrodes by:
applying respective stimulation currents to respective electrodes in temporally non-overlapping manner; and
obtaining data indicative of transimpedance at respective electrodes while the respective stimulation currents are applied.

25. The method of claim 24, further comprising:
automatically comparing the data indicative of transimpedance for the respective electrodes for the respective stimulation currents.

26. The method of claim 25, further comprising:
automatically developing weighting factors for the first electrodes based on the comparison of the data indicative of transimpedance for the respective first electrodes; and automatically determining which of the plurality of electrodes are to be disabled based on the weighting factors; and
automatically disabling the determined electrodes.

27. A method, comprising:
evaluating at least one of interactions of respective current spreads with one another or interactions of respective neural spreads with one another for a plurality of electrodes implanted in a recipient;
disabling or disadvantaging at least one electrode based on the evaluation;
applying electrical current to the electrodes of the plurality of electrodes to generate the respective current spreads and/or to evoke the neural spreads;
obtaining data indicative of respective current spreads for the electrodes by:
  applying respective stimulation currents to respective first electrodes in temporally non-overlapping manner; and
  obtaining data indicative of transimpedance at respective first electrodes while the respective stimulation currents are applied, wherein
the action of evaluating the at least one of interactions of respective current spreads with one another or interactions of respective neural spreads with one another for the plurality of electrodes implanted in a recipient includes comparing data indicative of the transimpedance for the respective electrodes for the respective currents applied to the electrodes of the plurality of electrodes, developing weighting factors for the respective electrodes based on the comparison of the data indicative of transimpedance for the respective electrodes.

28. The method of claim 27, wherein:
the electrodes are electrodes of a hearing prosthesis.

29. The method of claim 28, further comprising:
creating a map for the hearing prosthesis based on the evaluation, and
applying the map to the hearing prosthesis, wherein
the map, when applied, disadvantages the at least one electrode.

* * * * *